(12) United States Patent
Sundaram et al.

(10) Patent No.: US 8,569,262 B2
(45) Date of Patent: Oct. 29, 2013

(54) POLYSACCHARIDE COMPOSITIONS AND METHODS OF USE FOR THE TREATMENT AND PREVENTION OF DISORDERS ASSOCIATED WITH PROGENITOR CELL MOBILIZATION

(75) Inventors: Mallikarjun Sundaram, Flemington, NJ (US); Takashi Kei Kishimoto, Lexington, MA (US); Sucharita Roy, Tyngsboro, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 209 days.

(21) Appl. No.: 12/816,369

(22) Filed: Jun. 15, 2010

(65) Prior Publication Data

US 2010/0316640 A1 Dec. 16, 2010

Related U.S. Application Data

(63) Continuation-in-part of application No. 12/762,268, filed on Apr. 16, 2010, which is a continuation-in-part of application No. PCT/US2008/082223, filed on Nov. 3, 2008.

(60) Provisional application No. 60/985,123, filed on Nov. 2, 2007.

(51) Int. Cl.
*A61K 31/727* (2006.01)
*A61K 31/715* (2006.01)
*A01N 43/04* (2006.01)

(52) U.S. Cl.
USPC .............................. 514/56; 514/54

(58) Field of Classification Search
USPC .................................. 514/56, 54
See application file for complete search history.

(56) References Cited

U.S. PATENT DOCUMENTS

| | | | |
|---|---|---|---|
| 3,118,816 A | 1/1964 | Gushing et al. |
| 4,303,651 A | 12/1981 | Lindahl et al. |
| 4,629,699 A | 12/1986 | Bianchini |
| 4,717,719 A | 1/1988 | Sportoletti et al. |
| 4,727,063 A | 2/1988 | Naggi et al. |
| 4,847,338 A | 7/1989 | Linhardt et al. |
| 4,916,219 A | 4/1990 | Linhardt et al. |
| 4,990,502 A | 2/1991 | Lormeau et al. |
| 5,262,403 A | 11/1993 | Nicolson et al. |
| 5,264,425 A | 11/1993 | Dal Pozzo et al. |
| 5,296,471 A | 3/1994 | Holme et al. |
| 5,403,827 A | 4/1995 | De-Ambrosi |
| 5,541,166 A | 7/1996 | Parish et al. |
| 5,583,121 A | 12/1996 | Chaudry et al. |
| 5,668,116 A | 9/1997 | Cullis-Hill et al. |
| 5,668,118 A | 9/1997 | Kennedy |
| 5,690,910 A | 11/1997 | Ahmed et al. |
| 5,696,100 A | 12/1997 | Holme et al. |
| 5,707,974 A | 1/1998 | Kennedy |
| 5,763,421 A | 6/1998 | Caretto et al. |
| 5,767,269 A | 6/1998 | Hirsh et al. |
| 5,795,875 A | 8/1998 | Holme et al. |
| 5,808,021 A | 9/1998 | Holme et al. |
| 5,912,237 A | 6/1999 | Kennedy |
| 5,990,097 A | 11/1999 | Kennedy |
| 6,001,820 A | 12/1999 | Hirsh et al. |
| 6,077,683 A | 6/2000 | Kennedy |
| 6,127,347 A | 10/2000 | Chaudry et al. |
| 6,130,210 A | 10/2000 | Caretto et al. |
| 6,150,342 A | 11/2000 | Mattsson et al. |
| 6,545,136 B1 | 4/2003 | Hara et al. |
| 6,596,705 B1 | 7/2003 | Varki et al. |
| 7,781,416 B2 | 8/2010 | Casu et al. |
| 7,790,700 B2 | 9/2010 | Casu et al. |
| 8,067,555 B2 | 11/2011 | Casu et al. |
| 8,071,569 B2 | 12/2011 | Mousa |
| 2003/0013682 A1 | 1/2003 | Banito et al. |
| 2003/0147848 A1 | 8/2003 | Geng |
| 2005/0107331 A1 | 5/2005 | Banito et al. |
| 2005/0137167 A1 | 6/2005 | Casu et al. |
| 2005/0222084 A1 | 10/2005 | Casu et al. |
| 2005/0282775 A1 | 12/2005 | Kennedy |
| 2006/0040896 A1 | 2/2006 | Kennedy |
| 2006/0172968 A1 | 8/2006 | Casu et al. |
| 2007/0142323 A1 | 6/2007 | Viskov et al. |
| 2008/0051567 A1 | 2/2008 | Casu et al. |

FOREIGN PATENT DOCUMENTS

| | | |
|---|---|---|
| BE | 620906 | 11/1962 |
| EP | 0121067 A1 | 10/1984 |
| EP | 0346810 A2 | 12/1989 |
| EP | 0557887 A2 | 9/1993 |
| EP | 0735050 B1 | 10/1996 |
| EP | 1129718 A2 | 9/2001 |
| EP | 1268558 A1 | 1/2003 |
| WO | 9201003 A1 | 1/1992 |
| WO | 9202232 A1 | 2/1992 |

(Continued)

OTHER PUBLICATIONS

Definition of "prevention" from the Institute for International Medical Education [online], [Retrieved on Mar. 24, 2011]. Retrieved from the Internet <http://www.iime.org/glossary.htm>. Published Feb. 2002, p. 1, 2, 26, 27 and 39.*

"Metastasis." Encyclopædia Britannica. Encyclopædia Britannica Online Academic Edition. Encyclopædia Britannica Inc., 2011. Web. Dec. 6, 2011. <http://www.britannica.com/EBchecked/topic/378021/metastasis>.*

Johnson, R. Can Cancer Tumors Be Starved to Death? Retrieved Sep. 20, 2012 [online] <http://www.mhhe.com/biosci/genbio/tlw3/virtual_labs/lab6/labs/lab6/resources/original.pdf>.*

(Continued)

*Primary Examiner* — Scarlett Goon

(74) *Attorney, Agent, or Firm* — Lando & Anastasi LLP

(57) ABSTRACT

Polysaccharide preparations lacking substantial anticoagulant activity are provided herein. Methods of making and using such preparations are provided.

46 Claims, 8 Drawing Sheets

(56) References Cited

FOREIGN PATENT DOCUMENTS

| WO | 9217187 A1 | 10/1992 |
| WO | 9217188 A1 | 10/1992 |
| WO | 9218545 A1 | 10/1992 |
| WO | 9629973 A2 | 10/1996 |
| WO | 0155221 A1 | 8/2001 |
| WO | 03022291 A1 | 3/2003 |
| WO | 2007056218 A2 | 5/2007 |
| WO | 2009007224 A1 | 1/2009 |
| WO | 2009059283 A1 | 5/2009 |

OTHER PUBLICATIONS

Mao, W., Thanawiroon, C., Linhardt, R.J. (2002) Capillary electrophoresis for the analysis of glycosaminoglycans and glycosaminoglycan-derived oligosaccharides. Biomedical Chromatography, vol. 16, p. 77-94.*

Goodman and Gilman's The Pharmacological Basis of Therapeutics. editors Joel G. Hardman and Lee E. Limbird, published by The McGraw-Hill Companies, Inc., 2001, p. 5-8.*

Casu et al., "Chemical Derivatization as a Strategy to Study Structure-Activity Relationships of Glycosaminoglycans", Seminars in Thrombosis and Hemostasis, Col. 28, No. 4, pp. 335-342 (2002).

Casu et al., "Non-Anticoagulant Heparins and Inhibition of Cancer", Pathophysiol Haemost Thromb., vol. 36, pp. 195-203 (2007).

Casu et al., "Retention of Antilipemic Activity by Periodate-oxidized Non-anticoagulant Heparins", Arseneimittel Forschung/Drug Res. vol. 36 (1), No. 4, pp. 637-642 (1986).

Casu et al., "Short Heparin Sequences Spaced by Glycol-Split Uronate Residues Are Antagonists of Fibroblast Growth Factor 2 and Angiogenesis Inhibitors", Biochemistry, vol. 41, pp. 10519-10528 (2002).

Casu et al., "Undersulfated and Glycol-Split Heparins Endowed with Antiangiogenic Activity", J. Med. Chem., vol. 47, pp. 838-848 (2004).

Fransson et al., "Relationship between anticoagulant activity of heparin and susceptibility to periodate oxidation", Department of Physiological Chemsitry, vol. 97, No. 1, pp. 119-123 (1979).

Hrivocíni, et al., "Active Conformation of Glycosaminoglycans. NMR Determination of the Conformation of Heparin Sequences Complexed with Antithrombin and Fibroblast Growth Factors in Solution", Seminars in Thrombosis and Hemostasis, vol. 28, No. 4, pp. 325-333 (2002).

Icli et al., "Low moelecular weight heparin (LMWH) increase the efficacy of cisplatinum plus gemcitabine combination in advanced pancreatic cancer", J. Surg Oncol., vol. 95 (6), pp. 507-512 (2007) Abstract Only.

International Preliminary Report on Patentability for PCT/US2008/082223 filed Nov. 3, 2008.

International Search Report for PCT/US2008/082223 mailing date Jan. 28, 2009.

International Search Report for PCT/US2011/32581 date Jul. 5, 2011.

Kragh et al., "Non-anti-coagulant heparin inhibits metastasis but not primary tumor growth", Oncology Reports, vol. 14, pp. 99-104 (2005).

Mascellani et al., "Structure and Contribution to the heparin cofactor II-mediated inhibition of thrombin of naturally oversulphated sequences of dermatan sulphate" Biochem. J. vol. 296 pp. 639-648 (1993).

Naggi et al., "Modulation of the Heparanase-inhibiting Activity of Heparin through Selective Desulfation, Graded N-Acetylation, and Glycol Splitting", The Journal of Biological Chemistry, vol. 280, No. 13, pp. 12103-12113 (2005).

Peters et al., "Randomized comparison of a novel anticoagulant, vasoflux, and heparin as adjunctive therapy to streptokinase for acute myocardial infarction(vasoflux international trial for acute myocardial infarction lysis)", American Heart Journal., vol. 142 (2), pp. 237-243 (2001).

Pisano et al., "Undersulfated, low-molecular-weight glycol-split heparin as an antiangiogenic VEGFantagonist" Glycobiology, vol. 15, No. 2, pp. 1C-6C. (2005).

Ritchie et al., "A chemically modified heparin, inhibits myeloma growth and angiogenisis via disruption of the heparanase/syndecan-1 axis", Clin Can Res, pp. 1382-1393 (2011).

Sasisekharan et al., "Roles of Heparin-Sulphate Glycosaminoglycans in Cancer", Nature Reviews, vol. 2, pp. 521-528 (2002).

Spickler et al., "Clinical evaluation of the pharmacology, and safety of vasoflux[trademark symbol], a novel antithrombotic", Abstracts from the 70th scientific sessions, Nov. 9-12, 1997.

Weitz et al., "Vasoflux, a new anticoagulant with a novel mechanism of action", circ.ahajournals.org, pp. 682-689 (1999).

Written Opinion of the International Seaching Authority for PCT/US2011/32851 mailing date Jul. 5, 2011.

Written Opinion of the International Seraching Authority for PCT/US2008/082223, mailing date Jan. 28, 2009.

Yang et al., "Targeting heparanase as a therapy for multiplemyeloma", Abstract # 257, Apr. 18, 2009.

He Zhou et al., "M-ONC 402-a non anticoagulant low molecular weight heparin inhibits tumor metastasisHe", Proceedings of the American Association for Cancer Research Annual Meeting, p. 69 (2009).

Extended European Search Report from European Application No., 11769624.5 dated Jun. 26, 2013.

* cited by examiner

POLYSACCHARIDE COMPOSITIONS AND METHODS OF USE FOR THE TREATMENT AND PREVENTION OF DISORDERS ASSOCIATED WITH PROGENITOR CELL MOBILIZATION

This application is a continuation-in-part of and claims priority to U.S. Ser. No. 12/762,268, filed Apr. 16, 2010, which is a continuation-in-part of and claims priority to PCT Application No.: PCT/US2008/082223, filed Nov. 3, 2008, which claims priority to U.S. provisional application Ser. No. 60/985,123, filed Nov. 2, 2007. The disclosures of the prior applications are considered part of (and are incorporated by reference in) the disclosure of this application.

BACKGROUND

Heparin, a highly sulfated heparin-like glycosaminoglycan (HLGAG) produced by mast cells and isolated from natural sources, is a widely used clinical anticoagulant. However, the effects of natural, or unfractionated, heparin can be difficult to predict and patients must be monitored closely to prevent over- or under-anticoagulation. Low molecular weight heparins (LMWHs) obtained by various methods of fractionation or depolymerization of polymeric heparin have more predictable pharmacological action as anticoagulants, reduced side effects, sustained antithrombotic activity, and better bioavailability than unfractionated heparin (UFH). Several LMWHs are approved for outpatient treatment of thrombotic conditions.

There is increasing interest in the potential role of antithrombotic agents in the management of cancer patients. Results from several recent clinical trials have suggested a survival advantage for certain types of cancer patients treated with LMWHs (reviewed in Lemoine, 2005, *Journal of Clinical Oncology*, 23: 2119-20).

SUMMARY OF THE INVENTION

The invention is based, in part, on the development of polysaccharide preparations, e.g., preparations of polysaccharides derived from heparin, that lack substantial anticoagulant activity (e.g., preparations of polysaccharides that have reduced anticoagulant activity) but retain activity in other non-coagulation mediated biological processes. These compounds can have one or more of the following features: 1) anti-Xa activity, e.g., less than 50 IU/mg, 20 IU/mg, 10 IU/mg, 5 IU/mg or less, and 2) anti-metastatic, anti-angiogenic, anti-fibrotic and/or anti-inflammatory activity. A polysaccharide preparation provided herein can also have one or more of the following characteristics: the preparation has glycol split uronic acid residues (e.g., less than 50%, 40%, 30%, 20% glycol split uronic acid residues); the preparation has no more than 3 glycol split uronic acid residues ($U_G$) per polysaccharide chain; the preparation has greater than 40% $U_{2S}H_{NS,6S}$ disaccharide residues; degree of desulfation of the preparation is less than 40% (e.g., the degree of N-desulfation is less than 40%); one or more polysaccharide chains in the preparation have a 4,5-unsaturation of a non-reducing end uronic acid residue; one or more polysaccharide chains in the preparation have a 2,5-anhydromannitol residue at the reducing end; the weight average molecular weight of the preparation is between 3,500 and 8,000 Da, e.g., between 4,000 and 8,000 Da; and a molecular weight distribution described herein. This disclosure includes preparations having one or more of these properties and characteristics as well as methods of making and using such preparations.

Accordingly, in a first aspect, the invention features a polysaccharide preparation (e.g., a heparin-derived preparation) having the following characteristics: (a) a weight average molecular weight between 3,500 and 8,000 Da, e.g., a weight average molecular weight described herein; (b) anti-Xa activity and/or anti-IIa activity, e.g., less than 50 IU/mg (e.g., anti-Xa activity less than about 40 IU/mg, 30 IU/mg, 20 IU/mg, 15 IU/mg, 10 IU/mg, 5 IU/mg, 4 IU/mg or 3 IU/mg and anti-IIa activity less than about 40 IU/mg, 30 IU/mg, 20 IU/mg, 10 IU/mg, 5 IU/mg, 4 IU/mg, or 3 IU/mg); and (c) less than 50% glycol split uronic acid residues (e.g., less than 40%, 30%, 25%, or 20% glycol split uronic acid residues but more than 1%, 5%, 10%, 15%) in the preparation. In some embodiments, the preparation contains between 5% and 50% glycol split uronic acid residues (e.g., between 5% and 40%, 5% and 30%, 10% and 50%, 10% and 40%, 10% and 30%, or 10 and 20% glycol split uronic acid residues). In some embodiments, the preparation has a molecular weight distribution described herein.

In a second aspect, the invention features a polysaccharide preparation (e.g., a heparin-derived preparation) having the following characteristics: (a) a weight average chain molecular weight between 3,500 and 8,000 Da, e.g., a weight average molecular weight described herein; (b) anti-Xa activity and/ or anti-IIa activity each less than 50 IU/mg (e.g., anti-Xa activity less than about 40 IU/mg, 30 IU/mg, 20 IU/mg, 15 IU/mg, 10 IU/mg, 5 IU/mg, 4 IU/mg, 3 IU/mg and/or anti-IIa activity less than about 40 IU/mg, 30 IU/mg, 20 IU/mg, 10 IU/mg, 5 IU/mg, 4 IU/mg, or 3 IU/mg); and (c) the polysaccharide chains of the preparation have no more than 3 glycol split uronic acid residues ($U_G$) per polysaccharide chain (e.g., each polysaccharide chain has no more than 2 or no more than 1 glycol split uronic acid residue ($U_G$) per polysaccharide chain). The polysaccharide preparation includes one or more chains having a glycol split uronic acid residue ($U_G$). In some embodiments, the preparation has a molecular weight distribution described herein.

In a third aspect, the invention features a polysaccharide preparation (e.g., a heparin-derived preparation) having the following characteristics: (a) a weight average chain molecular weight between 3,500 and 8,000 Da, a weight average molecular weight described herein; (b) anti-Xa activity and anti-IIa activity, e.g., each less than 50 IU/mg (e.g., anti-Xa activity less than about 40 IU/mg, 30 IU/mg, 20 IU/mg, 15 IU/mg, 10 IU/mg, 5 IU/mg, 4 IU/mg, 3 IU/mg and anti-IIa activity less than about 40 IU/mg, 30 IU/mg, 20 IU/mg, 10 IU/mg, 5 IU/mg, 4 IU/mg, or 3 IU/mg); and (c) polysaccharide chains of the preparation have on average no more than 3 glycol split uronic acid residues ($U_G$) per polysaccharide chain (e.g., on average no more than 2.5, no more than 2, no more than 1.5, or no more than 1 glycol split uronic acid residues ($U_G$) per polysaccharide chain. In some embodiments, the preparation has a molecular weight distribution described herein.

In a fourth aspect, the invention features a polysaccharide preparation (e.g., a heparin-derived preparation) having the following characteristics: (a) a weight average chain molecular weight between 3,500 and 8,000 Da, e.g., a weight average molecular weight described herein; (b) anti-Xa activity and anti-IIa activity, e.g., each less than 50 IU/mg (e.g., anti-Xa activity less than about 40 IU/mg, 30 IU/mg, 20 IU/mg, 15 IU/mg, 10 IU/mg, 5 IU/mg, 4 IU/mg, 3 IU/mg and anti-IIa activity less than about 40 IU/mg, 30 IU/mg, 20 IU/mg, 10 IU/mg, 5 IU/mg, 4 IU/mg, or 3 IU/mg); and (c) the preparation has greater than 40% $U_{2S}H_{NS,6S}$ disaccharide residues (e.g., greater than 50%, 60%, 70%, or 80% $U_{2S}H_{NS,6S}$ disaccharide residues). In some embodiments, the preparation has a degree of desulfation less than 40% (e.g., less than 30%, 20%, or 10%). In some embodiments, the preparation has a degree of N-desulfation, 6-O desulfation and/or 2-O desulfation of less than 40%, less than 30%, less than 20%, less than 10%, less than 5%, less than 2%, less than 1%. In some embodiments, the degree of N-desulfation and 6-O desulfation is less than 40%, less than 30%, less than 20%, less than 10%, less than 5%, less than 2%, less than 1%. In some embodiments, the degree of 6-O desulfation is greater than the level of N-desulfation. In some embodiments, the degree of N-desulfation is less then 40%, 30%, 20%, 10%, 5%, 4%, 3%, 2%, 1%, the degree of 6-0 desulfation is less than 40%, 30%, 20%, 10%, 5%, and the degree of 6-O desulfation is greater than the degree of N-desulfation. For example, in one embodiment the degree of N-desulfation is less than 5%, 4%, 3%, 2%, 1% and the degree of 6-0 desulfation is greater than 5%, 6%, 7%, 8%, 9%, 10%, 15%. In some embodiments, the preparation has a molecular weight distribution described herein.

In a fifth aspect, the invention features a polysaccharide preparation (e.g., a heparin-derived preparation) lacking substantial anticoagulant activity (e.g., having reduced anticoagulant activity), wherein the preparation includes polysaccharides that include Formula I:

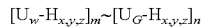

wherein U indicates a uronic acid residue and H indicates a hexosamine residue;

m and n are integers such that
m=4-16 (e.g., 4-8, 4-9, 4-10, 4-11, 4-12, 4-13, 4-14, or 4-15), and
n=1-4 (e.g., 1-2 or 1-3);
w=-2OS or -2OH;
x=—NS or —NAc;
y=-3OS or -3OH;
z=-6OS or -6OH;
and

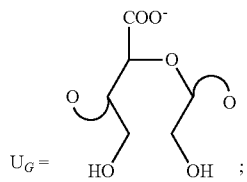

wherein the symbol ~ indicates that the units marked m and n are distributed along the polysaccharide chain and are not necessarily in sequence. For example, the following polysaccharide chain is encompassed by this embodiment:

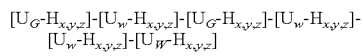

In addition, each of w, x, y, and z can be the same or different for each occurrence of $[U_w\text{-}H_{x,y,z}]$, and each of x, y, and z can be the same or different for each occurrence of $[U_G\text{-}H_{x,y,z}]$. Each occurrence of U can independently be an iduronic acid (I) or a glucuronic acid (G). In some embodiments, the preparation has anti-Xa activity of less than 50 IU/mg, 40 IU/mg, 30 IU/mg or 20 IU/mg but greater than 0.1 IU/mg, 0.5 IU/mg, 1 IU/mg or 2 IU/mg and/or anti-IIa activity of less than 50 IU/mg, 40 IU/mg, 30 IU/mg or 20 IU/mg but greater than 0.1 IU/mg, 0.5 IU/mg, 1 IU/mg or 2 IU/mg). In some embodiments, the preparation has a molecular weight distribution described herein.

In a sixth aspect, the invention features a polysaccharide preparation (e.g., a heparin-derived preparation) lacking substantial anticoagulant activity (e.g., having substantially no anticoagulant activity) and having antimetastatic activity, wherein the preparation includes polysaccharides that include Formula II:

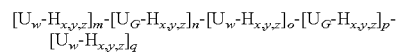

wherein U indicates a uronic acid residue and H indicates a hexosamine residue;

wherein m-r are integers such that:
m=0-10;
n=0-3;
o=0-10;
p=0-3;
q=0-10;
w=-2OS or -2OH;
x=—NS or —NAc;
y=-3OS or -3OH;
z=-6OS or -6OH;
and

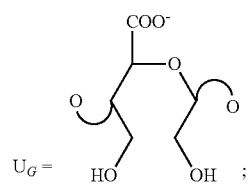

In some embodiments, the sum of n and p is 4, 3, 2 or 1. In some embodiments, the sum of m, o and q is between 4 and 18, e.g., 4-8, 4-9, 4-10, 4-11, 4-12, 4-13, 4-14, 4-15, 4-16 or 4-17.

In addition, each of w, x, y, and z can be the same or different for each occurrence of $[U_w\text{-}H_{x,y,z}]$, and each of x, y, and z can be the same or different for each occurrence of $[U_G\text{-}H_{x,y,z}]$. Each occurrence of U can independently be an iduronic acid (I) or a glucuronic acid (G).

In some embodiments, the preparation has anti-Xa activity of less than 50 IU/mg, 40 IU/mg, 30 IU/mg or 20 IU/mg but greater than 0.5 IU/mg, 1 IU/mg or 2 IU/mg and/or anti-IIa activity of less than 50 IU/mg, 40 IU/mg, 30 IU/mg or 20 IU/mg but greater than 0.5 IU/mg, 1 IU/mg or 2 IU/mg). In some embodiments, the preparation has a weight average chain molecular weight between 3,500 and 8,000 Da, e.g., between 4,000 and 7000 Da, 4,500 and 7,000 Da, 4,700 and 7,000 Da and 5,000 and 7,000 Da. In some embodiments, the preparation has a molecular weight distribution described herein.

The invention also includes pharmaceutically acceptable salts of any of the preparations described herein (e.g., described above) and compositions (e.g., pharmaceutical compositions) that comprise the preparations described herein and/or their pharmaceutically acceptable salts.

Any of the preparations described herein, e.g., described above, can have other properties. E.g., one of the above described preparations or pharmaceutical compositions can further have one or more of the functional or structural properties set out below.

In one embodiment, at least one of the polysaccharide chains in the preparation has one of the following structures at the non-reducing end:

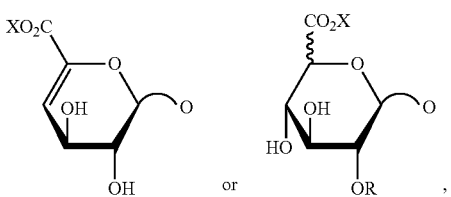

wherein X is H or Me and R is H or SO₃. For example, about 10%, 20%, 30%, 40%, 50%, 60%, 70%, 80%, 90%, or substantially all of the non-reducing ends of the preparation or pharmaceutical composition have the structure.

In one embodiment, at least one of the polysaccharide chains in the preparation or pharmaceutical composition includes a 2,5-anhydromannitol residue at the reducing end. For example, about 10%, 20%, 30%, 40%, 50%, 60%, 70%, 80%, 90%, or substantially all of the polysaccharide chains in the preparation or pharmaceutical composition include a 2,5-anhydromannitol residue at the reducing end.

In one embodiment, the preparation or pharmaceutical composition has a molecular weight distribution such that 10-50% (e.g., 10-40%, 10-30%, 15-30% or 15-25%) of the oligosaccharides of the preparation have a molecular weight <3000 Da; 40-65% (e.g., 40-60%, 45-65%, 50-65%, or 55-65%) of the oligosaccharides have a molecular weight between 3000-8000 Da, and 5-30% (e.g., 10-30%, 15-30%, 10-25%, or 15-25%) of the oligosaccharides have a molecular weight >8000 Da.

In one embodiment, the preparation has a polydispersity of about 1.2 to 1.7 (e.g., about 1.3 to 1.7, 1.4 to 1.6, or 1.3 to 1.6).

In one embodiment, the preparation or composition has anti-metastatic activity.

In one embodiment, the preparation or composition binds specifically to or inhibits an activity of one or more of: VEGF, FGF, SDF-1-α, HB-EGF, heparanase, SCF, sonic hedgehog, osteopontin, osteopontegerin or P-selectin.

In one embodiment, the preparation or composition has a sodium content less than 30%, 25%, 20%, 15%, 10%. In one embodiment, the preparation or composition comprises: less than 20 ppm, 15 ppm, 10 ppm, 5 ppm iodine; less than 30%, 25%, 20%, 15%, 10% sulfur; less than 50, 40, 30, 20, 15 ppm boron.

In one embodiment, any preparation or composition described herein is manufactured using good manufacturing practices (GMP) as defined by the U.S. Food and Drug Administration (21 CFR Part 110).

In another aspect, the invention features methods of making a preparation. The methods include: combining UFH and nitrous acid (HONO) to produce a polysaccharide preparation; and, following nitrous acid treatment, performing reactions to produce a glycol split of at least a portion of the uronic acid residues in the preparation.

In another aspect, methods of making a preparation include: depolymerizing an UFH (e.g., by chemical hydrolysis or enzymatic depolymerization); and, following depolymerization, performing reactions to produce a glycol split of at least a portion of the uronic acid residues in the preparation.

In one embodiment, reactions to produce a glycol split of at least a portion of the uronic residues in the preparation include oxidizing the polysaccharide preparation with periodate; and reducing the oxidized polysaccharide preparation with sodium borohydride. For example, the methods include oxidizing the polysaccharide preparation with periodate for about 10-20 hours at a temperature of about 0-10° C.; and following oxidation, reducing the sample with sodium borohydride for about 1 hour at a pH of about 5.0-8.0 at a temperature of about 0-10° C.

In another aspect, the invention features methods of manufacturing a preparation. The methods include: (1) depolymerizing an unfractionated heparin (UFH) (e.g., by nitrous acid depolymerization, hydrolytic depolymerization, or enzymatic depolymerization) to yield a polysaccharide preparation; (2) oxidizing the polysaccharide preparation with periodate; (3) reducing the oxidized polysaccharide preparation with sodium borohydride; and (4) isolating the polysaccharide preparation (e.g., by precipitating with a salt and a polar organic solvent, or by subjecting to a chromatographic separation or purification), to thereby make a preparation.

In one embodiment, the step of depolymerizing includes treating the UFH with about 0.01 to 0.05 M (e.g., about 0.02 to 0.04 M) nitrous acid at a pH of about 2 to 4 for about 1 to 5 hours at a temperature of about 10 to 30° C.

In one embodiment, the step of oxidizing includes treating the polysaccharide preparation with about 0.05 to 0.2 M periodate for about 10 to 20 hours at a temperature of about 0 to 10° C.

In one embodiment, the step of reducing comprises treating the oxidized polysaccharide preparation with about 0.5 to 2.0% (w/v) sodium borohydride for about 0.5 to 3 hours at a pH of about 6.0 to 7.0 and a temperature of about 0 to 10° C.

In one embodiment, a method of making or manufacturing a polysaccharide preparation includes reducing the amount of boron in the preparation.

In one embodiment, the steps in a method of manufacture described are performed using good manufacturing practices (GMP) as defined by the U.S. Food and Drug Administration (21 CFR Part 110).

In one embodiment, the preparation is evaluated for a biological activity, e.g., anti-metastatic activity; binding to any of VEGF, FGF, SDF-1α, HB-EGF, heparanase and P-selectin; or inhibition of an activity of any of VEGF, FGF, SDF-1α, and P-selectin.

The degree of desulfation, as used herein, is defined as the percent reduction in moles of sulfate per moles of disaccharide unit as compared to unfractionated heparin.

The degree of sulfation, as used herein, is defined as the average number of moles of sulfate per moles of disaccharide unit.

In another aspect, the invention features a polysaccharide preparation made by a method described herein.

In another aspect, the invention includes an intermediate or reaction mixture from any of the methods for making or analyzing a polysaccharide preparation described herein.

In another aspect, the invention features a pharmaceutical composition that includes a polysaccharide preparation described herein.

In one embodiment, the pharmaceutical composition further includes a pharmaceutically acceptable carrier.

In another aspect, the invention features a method of treating a subject that includes administering a therapeutically effective amount of a polysaccharide preparation disclosed herein to the subject. The terms "treating", "treatment", and the like, mean administering the preparation to a subject or a cell or tissue of a subject in order to obtain a desired pharmacological, physiological or clinical effect. Treatment with a polysaccharide preparation described herein may lessen, reduce, mitigate, ameliorate, delay, or prevent an existing unwanted condition or the onset or a symptom thereof. A "therapeutically effective amount" refers to an amount effective, at dosages and for periods of time necessary, to achieve the desired pharmacological, physiological or clinical effect in the subject.

The invention includes methods for treating a subject having, or at risk of having, a metastatic disorder (e.g., a cancer, e.g., a carcinoma or other solid and hematological cancer). In those subjects, treatment may include, but is not limited to, inhibited tumor growth, reduction in tumor mass, reduction in size or number of metastatic lesions, inhibited development of new metastatic lesions, prolonged survival, prolonged progression-free survival, prolonged time to progression, and/or enhanced quality of life. In another embodiment, the subject may have a disorder or condition selected from the group consisting of: an inflammatory disorder, an autoimmune disease, a fibrotic or fibroproliferative disorder or an atopic disorder. Examples of inflammatory disorders include but are not limited to chronic obstructive pulmonary disease, cystic fibrosis, asthma, rheumatoid arthritis, inflammatory bowel disease (including Crohns disease and ulcerative colitis), multiple sclerosis, psoriasis, ischemia-reperfusion injuries, septic shock, age-related macular degeneration (e.g., wet age-related macular degeneration), atherosclerosis, Alzheimer's disease, cardiovascular disease, vasculitis, type I and II diabetes, metabolic syndrome, diabetic retinopathy, restenosis. Examples of autoimmune diseases include but are not limited to asthma, rheumatoid arthritis, inflammatory bowel disease, multiple sclerosis, psoriasis, type I diabetes, systemic lupus erythematosus (SLE), Sjögren's syndrome, Hashimoto's thyroiditis, Graves' disease, Guillain-Barré syndrome, autoimmune hepatitis, Myasthenia gravis. Examples of fibrotic diseases include but are not limited to scleroderma, chronic obstructive pulmonary disease, diabetic nephropathy, sarcoidosis, idiopathic pulmonary fibrosis, liver fibrosis, pancreatic fibrosis, cirrhosis, cystic fibrosis, neurofibromatosis, endometriosis, post-operative fibroids, restenosis. Examples of atopic disease include but are not limited to atopic dermatitis, atopic asthma, and allergic rhinitis. The compositions of the invention are administered to a subject having or at risk of developing one or more of the diseases in an effective amount for treating the disorder or condition.

In a preferred embodiment, the subject has, or is at risk of having, a cancer or metastatic disorder (e.g., a carcinoma). For example, the subject has a primary tumor and has, or is at risk of having, a metastasis of that primary tumor.

In one embodiment, the polysaccharide preparation is administered intravenously or subcutaneously or is inhaled.

In one embodiment, the polysaccharide preparation is administered in combination with another therapy, e.g., another therapeutic agent, e.g., a cytotoxic or cytostatic agent, and combinations thereof.

In one embodiment, the polysaccharide preparation is administered chronically, e.g., at least twice over a specific period of time, e.g., at least twice during a period of six months. In one embodiment, a polysaccharide preparation is administered twice over a period of one week, two weeks, three weeks, one month, two months, three months, six months, one year, or even longer. The polysaccharide preparation can be administered daily (e.g., once, twice, or three or four times daily), once every other day, weekly (e.g., once, twice, or three times a week), once every other week, once every three weeks, monthly, or any other chronic administration schedule.

In one aspect, the invention includes methods of treating or preventing a disorder which involves or results from bone marrow derived progenitor cell mobilization. The method includes administering a polysaccharide preparation described herein, e.g., a polysaccharide preparation that lacks substantial anticoagulation activity, to a subject having or at risk of having the disorder or condition.

In one embodiment, the disorder or condition involves or results from mobilization of one or more of: endothelial progenitor cells (EPCs), hematopoietic progenitor cells (HPCs), immature myeloid cells (iMC, including myeloid derived suppressor cells (MDSC) and mesenchymal progenitor cells (MPC). In a preferred embodiment, the subject has, or is at risk of having, a cancer or metastatic disorder (e.g., a carcinoma). For example, the subject has a primary tumor and has, or is at risk of having, a metastasis of the primary tumor. In one embodiment, the subject has been or will be treated with a chemotherapeutic agent that is associated with increased bone marrow derived progenitor cell mobilization, e.g., increased EPC, HPC, iMC and/or mesenchymal progenitor cell mobilization. The chemotherapeutic agent can be, e.g., a taxane (e.g., paclitaxel, docetaxel, larotaxel, cabazitaxel); a pyrimidine analogue (e.g., fluorouracil); an epothilone (e.g., ixabepilone, epothilone B, epothilone D, dehydelone, sagopilone); a vascular disrupting agent (e.g., AVE8062, Oxi 4503, vadimezan, ZD6126, combretastatin A-4 disodium phosphate (CA4P), DMXAA (ASA404), NPI-2358); an alkylating agent (e.g., cyclophosphamide, dacarbazine, melphalan, ifosfamide, temozolomide); an anti-angiogenic agent or a tyrosine kinase inhibitor. In one embodiment, the anti-angiogenic agent or tyrosine kinase inhibitor selected from the group consisting of: an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a RAF-1 inhibitor and a RET inhibitor. In some embodiments, the subject has been treated or will be treated with an anti-angiogenic agent or a tyrosine kinase inhibitor selected from the group consisting of: bevacizumab (Avastin®), imatinib (Gleevec®), cetuximab (Erbitux®), sunitinib (Sutent®), sorafenib (Nexavar®), tivozanib (AV-951), cediranib (AZD2171), dasatinib (Sprycel®), nilotinib (AMN-107), CP-547632, erlotinib (Tarceva®), panitumumab (Vectibix®), pazopanib (Votrient®), axitinib and gefitinib (Iressa®), ranibizumab (Lucentis®).

In one embodiment, the subject has been or will be treated with a chemotherapeutic agent at a dose and/or dosing schedule that that is associated with increased bone marrow derived progenitor cell mobilization. For example, the chemotherapeutic agent is a taxane (e.g., paclitaxel, docetaxel, larotaxel, cabazitaxel) and the taxane is administered in an amount and/or at a dosing schedule that is associated with increased bone marrow derived progenitor cell (e.g., EPC) mobilization, e.g., a dose and/or dosing schedule described herein. In another embodiment, the chemotherapeutic agent is an anti-angiogenic agent or tyrosine kinase inhibitor (e.g., an anti-angiogenic agent or tyrosine kinase inhibitor described herein, e.g., sunitinib) and the anti-angiogenic agent or tyrosine kinase inhibitor is administered in an amount and/or at a dosing schedule that is associated with increased bone marrow derived progenitor cell (e.g., EPC) mobilization, e.g., a dose and/or dosing schedule described herein. In another embodiment, the chemotherapeutic agent is a pyrimidine analogue (e.g., fluorouracil) and the pyrimidine analogue is administered in an amount and/or at a dosing schedule that is associated with increased bone marrow derived progenitor cell (e.g., EPC) mobilization, e.g., a dose and/or dosing schedule described herein. In another embodiment, the chemotherapeutic agent is an anthracycline (e.g., doxorubicin) and the anthracycline is administered in an amount and/or at a dosing schedule that is associated with increased bone marrow derived progenitor cell (e.g., MDSC) mobilization, e.g., a dose and/or dosing schedule described herein.

In one embodiment, the subject has cancer and has been or will be administered a growth factor of blood cells in combination with a chemotherapeutic agent. Exemplary growth factors include granulocyte colony stimulating factor (GCSF), granulocyte macrophage colony stimulating factor (GM-CSF), and erythropoietin. In one embodiment, the polysaccharide preparation is administered after administration of the growth factor.

In another embodiment, the subject has cancer and has been or will be administered a CXCR4 antagonist, e.g., in combination with a chemotherapeutic agent.

In one embodiment, the cancer is a cancer described herein. For example, the cancer can be ovarian cancer, prostate cancer, lung cancer, liver cancer, breast cancer, glioma, gastric cancer, pancreatic cancer, head and neck cancer, colorectal cancer, esophageal squamous cell cancer, Kaposi's sarcoma, lymphoma, multiple myeloma, melanoma, thyroid carcinoma.

In another embodiment, the subject may have a disorder or condition selected from the group consisting of: an inflammatory disorder, an autoimmune disease, a fibrotic or fibroproliferative disorder, a vascular disorder. Examples of inflammatory disorders include, but are not limited to, chronic obstructive pulmonary disease, asthma, rheumatoid arthritis, inflammatory bowel disease (including Crohns disease and ulcerative colitis), multiple sclerosis, psoriasis, ischemia-reperfusion injuries, septic shock, age-related macular degeneration (e.g., wet age-related macular degeneration), atherosclerosis, Alzheimer's disease, cardiovascular disease, vasculitis, type I and II diabetes, metabolic syndrome, diabetic retinopathy, restenosis and eosinophilic esophagitis. Examples of autoimmune diseases include but are not limited to asthma, rheumatoid arthritis, inflammatory bowel disease, multiple sclerosis, psoriasis, type I diabetes, systemic lupus erythematosus (SLE), Sjögren's syndrome, Hashimoto's thyroiditis, Graves' disease, Guillain-Barré syndrome, autoimmune hepatitis, Myasthenia gravis. Examples of fibrotic diseases include but are not limited to scleroderma, chronic obstructive pulmonary disease, diabetic nephropathy, sarcoidosis, idiopathic pulmonary fibrosis, cirrhosis, cystic fibrosis, neurofibromatosis, endometriosis, post-operative fibroids, pulmonary fibrosis, uterine fibroids, restenosis. An example of a vascular disorder is hemangioma. The compositions of the invention are administered to a subject having or at risk of developing one or more of the disorders in an effective amount for treating the disorder or condition.

In another aspect, the invention features a polysaccharide preparation described herein, e.g., a polysaccharide preparation the lacks substantial anticoagulation activity described herein, for use in a method of treatment described herein. In one embodiment, the polysaccharide preparation can be used in any of the methods described herein for treating or preventing a disorder which involves or results from bone marrow derived progenitor cell mobilization.

In another aspect, the invention features the use of a polysaccharide preparation described herein, e.g., a polysaccharide preparation that lacks substantial anticoagulation activity as described herein, for manufacture of a medicament for treating or preventing a disorder described herein, e.g., for treating or preventing a disorder which involves or results from bone marrow derived progenitor cell mobilization as described herein.

In another aspect, the invention features the use of a chemotherapeutic agent for the manufacture of a medicament for treating or preventing a disorder which involves or results from bone marrow derived progenitor cell mobilization as described herein, wherein the medicament is to be administered in combination with a polysaccharide preparation described herein, e.g., a polysaccharide preparation that lacks substantial anticoagulation activity as described herein.

In another aspect, the invention features a method of selecting a payment class for a course of treatment with a chemotherapeutic agent that is associated with bone marrow derived progenitor cell mobilization for a subject, e.g., a human subject, having cancer, e.g., a cancer described herein, comprising:

determining whether or not the subject is or will be receiving a chemotherapeutic agent that is associated with bone marrow derived progenitor cell mobilization; and assigning the subject to one of a plurality of payment classes if the subject is receiving a chemotherapeutic agent that is associated with bone marrow derived progenitor cell mobilization wherein:

a first payment class authorizes payment for treatment of the subject with the chemotherapeutic agent in combination with a polysaccharide preparation described herein, and a second payment class authorizes payment for treatment of the subject with the chemotherapeutic agent without a polysaccharide preparation described herein.

In some embodiments, assignment of the subject is to the first class and the assignment authorizes payment for a course of treatment (e.g., the chemotherapeutic agent and/or a polysaccharide preparation described herein).

In some embodiments, assignment of the subject is to the second class and the assignment authorizes a different payment for a course of treatment (e.g., a chemotherapeutic agent in the absence of a polysaccharide preparation described herein).

In some embodiments, the method further comprises determining if the subject has experienced a side effect from the chemotherapeutic agent.

In some embodiments, the chemotherapeutic agent can be, e.g., a taxane (e.g., paclitaxel, docetaxel, larotaxel, cabazitaxel); a pyrimidine analogue (e.g., fluorouracil); an epothilone (e.g., ixabepilone, epothilone B, epothilone D, dehydelone, sagopilone); a vascular disrupting agent (e.g., AVE8062, Oxi 4503, vadimezan, ZD6126, combretastatin A-4 disodium phosphate (CA4P), DMXAA (ASA404), NPI-2358); an alkylating agent (e.g., cyclophosphamide, dacarbazine, melphalan, ifosfamide, temozolomide); an anti-angiogenic agent or a tyrosine kinase inhibitor, e.g., an anti-angiogenic agent or tyrosine kinase inhibitor described herein.

For any of the ranges described herein, e.g., for a given structure or activity, the ranges can be those ranges disclosed as well as other ranges. For example, a range constructed from a lower endpoint of one range, e.g., for a given building block or activity, can be combined with the upper endpoint of another range, e.g., for the given building block or activity, to give a range.

An "isolated" or "purified" polysaccharide preparation is substantially free of cellular material or other contaminating proteins from the cell or tissue source from which the polysaccharide is derived, or substantially free from chemical precursors or other chemicals when chemically synthesized. "Substantially free" means that a preparation is at least 50% pure (wt/wt). In a preferred embodiment, the preparation has less than about 30%, 20%, 10% and more preferably 5% (by dry weight), of non-heparin-derived polysaccharides, proteins or chemical precursors or other chemicals, e.g., from manufacture. These are also referred to herein as "contaminants." Examples of contaminants that can be present in a polysaccharide preparation provided herein include, but are not limited to, sodium, sulfur, boron, enzyme (e.g., a heparinase enzyme), methanol, ethanol, iodine, and chloride.

"Combined use" or "in combination" as used herein means that the individual agents are administered concurrently or within a time interval such that the use of the combined agents provides an increased benefit (e.g., increased efficacy or decreased side effects) than if they were administered otherwise. In one embodiment, the individual agents are administered within an interval such that the physiological effects of the agents on the subject overlap. The term "payment class," as used herein, refers to payment plan correlated with a treatment regimen. The payment plan can be, e.g., payment for a treatment, a level of payment for a treatment, reimbursement for a treatment, a level of reimbursement for a treatment, denial of a payment for a treatment, denial of reimbursement for a treatment or denial of coverage for a treatment.

Other features and advantages of the invention will be apparent from the following detailed description, and from the claims.

DETAILED DESCRIPTION

Polyanions/Polysaccharides

Figure 1:
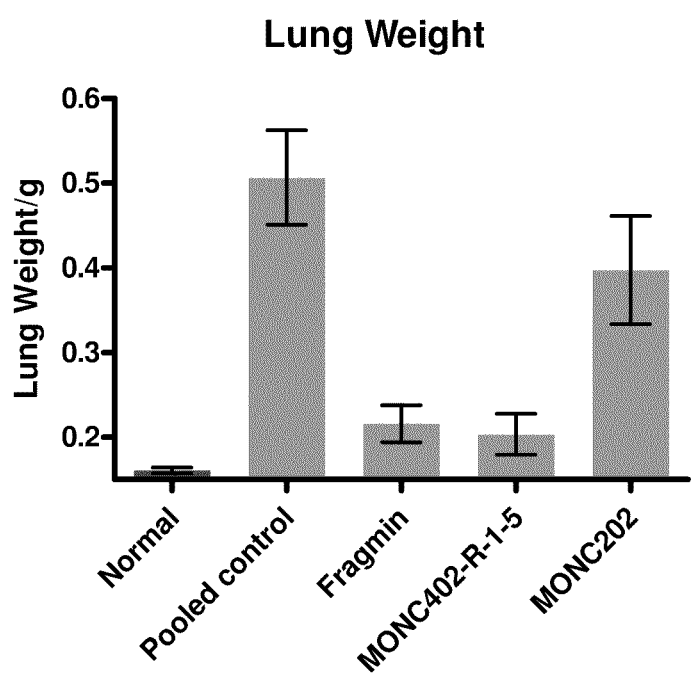
FIG. 1 is a bar graph showing the effect of a polysaccharide preparation described herein in a murine melanoma experimental metastasis (B16F10 i.v.) model. Lung tumor burden (lung weight—normal lung weight) was determined for female C57BL/6 mice (9-10 weeks old) challenged with i.v. injection of $2\times10^5$ B16F10 cells and pretreated with a single dose (10 mg/kg) of MONC402 (batch R-1-5), dalteparin (Fragmin®), or MONC 202 (negative control, N-desulfated polysaccharide) immediately before injection. "Normal" designates unchallenged and untreated mice.

The methods described herein relate to combination therapies including a polyanion such as a polysaccharide, glycosaminoglycan (GAGs), heparin, low molecular weight heparin, chemically or enzymatically modified heparin or heparin sulfate, heparan sulfate mimetic (e.g., PI-88), chemically or enzymatically synthesized polysaccharide, e.g., K5 polysaccharide. In one embodiment, the polyanion, polysaccharide, GAG, heparin, low molecular weight heparin, chemically or enzymatically modified heparin or heparan sulfate, heparan sulfate mimetic or chemically or enzymatically synthesized polysaccharide lacks substantial anticoagulant activity, i.e., exhibits less than 50 IU/mg of anti-IIa activity and less than 50 IU/mg of anti-Xa activity. In one embodiment, the polyanion, polysaccharide, GAG, heparin, low molecular weight heparin, chemically or enzymatically modified heparin or heparan sulfate, heparan sulfate mimetic or chemically or enzymatically synthesized polysaccharide exhibits residual anticoagulant activity, e.g., exhibits at least 0.1 IU/mg anti-IIa activity and at least 0.1 IU/mg anti-Xa activity, or at least 0.2 IU/mg anti-IIa activity and at least 0.2 IU/mg anti-Xa activity, or at least 0.5 IU/mg anti-IIa activity and at least 0.5 IU/mg anti-Xa activity, or at least 1 IU/mg anti-IIa activity and at least 1 IU/mg anti-Xa activity. In some embodiments, the polyanion, polysaccharide, GAG, heparin, low molecular weight heparin, chemically or enzymatically modified heparin or heparan sulfate, heparan sulfate mimetic or chemically or enzymatically synthesized polysaccharide exhibits 2 IU/mg, 3 IU/mg, 4 IU/mg, 5 IU/mg, 6 IU/mg, 7 IU/mg, 8 IU/mg, 9 IU/mg, 10 IU/mg, 12 IU/mg, 15 IU/mg, 18 IU/mg, 20 IU/mg, 22 IU/mg, 25 IU/mg, 28 IU/mg, 30 IU/mg of anti-IIa activity. In some embodiments, the polyanion, polysaccharide, GAG, heparin, low molecular weight heparin, chemically or enzymatically modified heparin or heparan sulfate, heparan sulfate mimetic or chemically or enzymatically synthesized polysaccharide exhibits 2 IU/mg, 3 IU/mg, 4 IU/mg, 5 IU/mg, 6 IU/mg, 7 IU/mg, 8 IU/mg, 9 IU/mg, 10 IU/mg, 12 IU/mg, 15 IU/mg, 18 IU/mg, 20 IU/mg, 22 IU/mg, 25 IU/mg, 28 IU/mg, 30 IU/mg of anti-Xa activity.

Heparin Preparations

In some aspects, the methods and kits described herein include a heparin preparation. A heparin preparation, as used herein, is a preparation which contains heparin or a preparation derived therefrom. Heparin preparations include unfractionated heparin preparations, low molecular weight heparin (LMWH) preparations, ultra low molecular weight heparin (ULMWH) preparations and the like.

The term "unfractionated heparin (UFH)" as used herein, is heparin purified from porcine intestinal mucosa. UFH can be used, e.g., as a starting material in the process to form a LMWH or an ULMWH. UFH is commercially available from several vendors including Abbott, Organon, Riker, Invenex, Baxter, Calbiochem, Sigma or Upjohn.

Examples of LMWH preparations include, but are not limited to, an enoxaparin preparation (Lovenox™ or Clexane™); a dalteparin preparation (Fragmin™); a certoparin preparation (Sandoparin™ or Embollex); an ardeparin preparation (Normiflo™); a nadroparin preparation (Fraxiparin™); a parnaparin preparation (Fluxum™); a reviparin preparation (Clivarin™); a tinzaparin preparation (Innohep™ or Logiparin™), a fondaparinux preparation (Arixtra™), or a M118-REH preparation. In some embodiments, the LMWH is a LMWH other than an enoxaparin preparation (Lovenox™ or Clexane™); a dalteparin preparation (Fragmin™); a certoparin preparation (Sandoparin™ or Embollex); an ardeparin preparation (Normiflo™); a nadroparin preparation (Fraxiparin™); a parnaparin preparation (Fluxum™); a reviparin preparation (Clivarin™); a tinzaparin preparation (Innohep™ or Logiparin™), a fondaparinux preparation (Arixtra™), or a M118-REH preparation.

Polysaccharide Preparations that Lack Substantial Anticoagulation Activity

In many clinical settings, commercially available LMWH preparations are preferred over UFH preparations as anticoagulants because LMWHs have more predictable pharmacokinetics and can be administered subcutaneously. However, because of the potential for bleeding complications due to their anticoagulant effects, currently available LMWH preparations are less suitable for therapy of non-coagulation mediated disorders, and/or for disorders that may require higher doses or chronic dosing regimens. The invention features polysaccharide preparations designed to lack substantial anticoagulant activity while retaining clinically advantageous properties. Properties of the polysaccharide preparations include, e.g., lacking substantial anticoagulant activity, e.g., anti-IIa activity less than 50 IU/mg, anti-Xa activity less than 50 IU/mg), and having anti-metastatic, anti-angiogenic, anti-fibrotic and/or anti-inflammatory activity.

Examples of such polysaccharide preparations include chains that include the following:

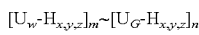

wherein U indicates a uronic acid residue and H indicates a hexosamine residue, wherein m and n are integers such that m=6-18, and n=1-4, w=-2OS or -2OH, x=—NS or —NAc, y=-3OS or -3OH, z=-6OS or -6OH, and

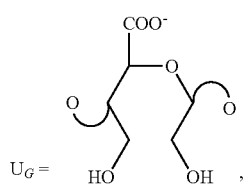

wherein the symbol ~ indicates that the units marked m and n are distributed along the polysaccharide chain and are not necessarily in sequence. For example, the following polysaccharide chain is encompassed by this embodiment:

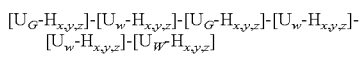

In addition, each of w, x, y, and z can be the same or different for each occurrence of $[U_w\text{-}H_{x,y,z}]$, and each of x, y, and z can be the same or different for each occurrence of $[U_G\text{-}H_{x,y,z}]$. Each occurrence of U can independently be an iduronic acid (I) or a glucuronic acid (G).

The polysaccharide preparation can have anti-Xa activity and anti-IIa activity each less than 50 IU/mg (e.g., anti-Xa activity less than about 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg); and

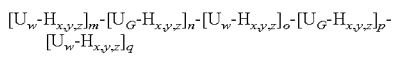

wherein U indicates a uronic acid residue and H indicates a hexosamine residue, wherein m-r are integers such that: m=0-10, n=0-3, o=0-10, p=0-3, q=0-10, w=-2OS or -2OH, x=—NS or —NAc, y=-3OS or -3OH, z=-6OS or -6OH, and

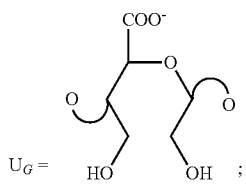

wherein w, x, y, and z are each the same or different on each unit marked m, n, o, p, or q. In some embodiments, the sum of n+p is less than or equal to 4 (e.g., less than or equal to 3, 2, 1, or 0). In some embodiments, the sum of n and p is 4, 3, 2 or 1. In some embodiments, the sum of m, o and q is between 4 and 18, e.g., 4-8, 4-9, 4-10, 4-11, 4-12, 4-13, 4-14, 4-15, 4-16 or 4-17.

In addition, each of w, x, y, and z can be the same or different for each occurrence of $[U_w\text{-}H_{x,y,z}]$, and each of x, y, and z can be the same or different for each occurrence of $[U_G\text{-}H_{x,y,z}]$. Each occurrence of U can independently be an iduronic acid (I) or a glucuronic acid (G).

The polysaccharide preparation can have anti-Xa activity and anti-IIa activity each less than 50 IU/mg (e.g., anti-Xa activity less than about 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg); and anti-IIa activity less than about 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg). In some embodiments, the preparation has a weight average chain molecular weight between 3,500 and 7,000 Da, e.g., 4,300 and 7000 Da, 4,500 and 7,000 Da, 4,700 and 7,000 Da and 5,000 and 7,000 Da.

Anti-IIa Activity

Polysaccharide preparations are disclosed herein that provide substantially reduced anti-IIa activity, e.g., e.g., anti-IIa activity of about less than about 50 IU/mg, less than about 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg). Anti-IIa activity is calculated in International Units of anti-IIa activity per milligram using statistical methods for parallel line assays. The anti-IIa activity levels described herein are measured using the following principle.

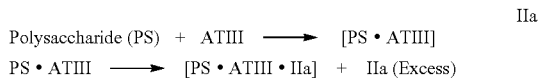

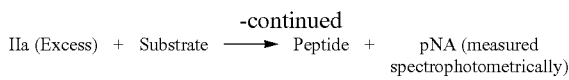

Anti-factor IIa activity is determined by the sample potentiating effect on antithrombin (ATIII) in the inhibition of thrombin. Thrombin excess can be indirectly spectrophotometrically measured. The anti-factor IIa activity can be measured, e.g., on a Diagnostica Stago analyzer or on an ACL Futura3 Coagulation system, with reagents from Chromogenix (S-2238 substrate, Thrombin (53 nkat/vial), and Anti-thrombin), or on any equivalent system. Analyzer response is calibrated using the 2nd International Standard for Low Molecular Weight Heparin.

Anti-Xa Activity

Preferably, a polysaccharide preparation provided herein has anti-Xa activity of about 0 to 50 IU/mg, e.g., 50 IU/mg, 40 IU/mg, 30 IU/mg, 20 IU/mg, 15 IU/mg, 10 IU/mg, 5 IU/mg, 4 IU/mg, 3 IU/mg, 2 IU/mg or 1 IU/mg; or from about 0 to 50 IU/mg, about 0 to 40 IU/mg, about 0 to 30 IU/mg, about 0 to 25 IU/mg, about 0 to 20 IU/mg, about 0 to 10 IU/mg, about 0 to 5 IU/mg, about 5 to 10 IU/mg, about 5 to 15 IU/mg, or about 5 to 20 IU/mg). Anti-Xa activity of a preparation is calculated in International Units of anti-factor Xa activity per milligram using statistical methods for parallel line assays. The anti-factor Xa activity of preparations described herein is measured using the following principle:

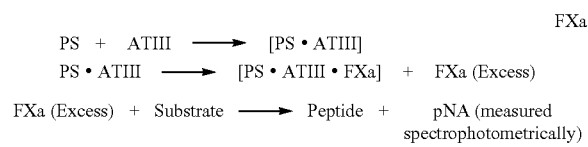

The anti-factor Xa activity is determined by the sample potentiating effect on antithrombin (ATIII) in the inhibition of activated Factor Xa (FXa). Factor Xa excess can be indirectly spectrophotometrically measured. Anti-factor Xa activity can be measured, e.g., on a Diagnostica Stago analyzer with the Stachrom® Heparin Test kit, on an ACL Futura3 Coagulation system with the Coatest® Heparin Kit from Chromogenix, or on any equivalent system. Analyzer response can be calibrated using the NIBSC International Standard for Low Molecular Weight Heparin.

Molecular Weight and Chain Length

When weight average molecular weight of a preparation is determined, a weight average molecular weight of about 3500 to 8000 Da, about 3500 to 7000 Da, preferably about 4000 to 7000 Da, about 4200 to 6000, or about 4500 to 6000 Da, indicates that a significant number of chains in the polysaccharide preparation are of sufficient chain length.

"Weight average molecular weight" as used herein refers to the weight average in daltons of chains of uronic acid/hexosamine disaccharide repeats. The presence of non-uronic acid and/or non-hexosamine building blocks are not included in determining the weight average molecular weight. Thus, the molecular weight of non-uronic acid and non-hexosamine building blocks within a chain or chains in the preparation should not be included in determining the weight average molecular weight. The weight average molecular weight ($M_w$) is calculated from the following equation: $M_w = \Sigma(c_i m_i)/\Sigma c_i$. The variable $c_i$ is the concentration of the polymer in slice i and $m_i$ is the molecular weight of the polymer in slice i. The summations are taken over a chromatographic peak, which contains many slices of data. A slice of data can be pictured as a vertical line on a plot of chromatographic peak versus time. The elution peak can therefore be divided into many slices. The weight average molecular weight calculation is average dependant on the summation of all slices of the concentration and molecular weight. The weight average molar weight can be measured, e.g., using the Wyatt Astra software or any appropriate software. The weight average molecular weights described herein are determined by high liquid chromatography with two columns in series, for example a TSK G3000 SWXL and a G2000 SWXL, coupled with a UV or multi angle light scattering (MALS) detector and a refractometric detector in series. The eluent used is a 0.2 M sodium sulfate, pH 5.0, and a flow rate of 0.5 mL/min.

A determination of whether a polysaccharide preparation includes chains of sufficient chain length can be made, for example, by determining the average chain length of the chains in the preparation and/or by determining the weight average molecular weight of chains within the preparation. When average chain length is determined, an average chain length of about 5 to 22, e.g., about 7 to 18, typically about 7 to 14 or 8 to 13 disaccharide repeats, indicates that a significant number of chains in the preparation are of sufficient chain length.

"Average chain length" as used herein refers to the average chain length of uronic acid/hexosamine disaccharide repeats that occur within a chain. The presence of non-uronic acid and/or non-hexosamine building blocks (e.g., attached PEG moieties) are not included in determining the average chain length. Average chain length is determined by dividing the number average molecular weight (Mn) by the number average molecular weight for a disaccharide (500 Da).

Glycol Split Uronic Acids

A polysaccharide preparation described herein can include an opening of the glycoside ring, conventionally called reduction-oxidation (RO) derivatives. In these preparations, one or more glycoside rings having vicinyl diols that are opened, e.g., at the bond between C2 and C3, by means of an oxidation action, followed by a reduction. The compounds referred to herein will also be called "Glycol Split" derivatives.

In a further embodiment of the invention described herein, the glycol split residues lend themselves to the subsequent functionalization. Therefore, the compounds may also bear equal or different groups, in place of the primary hydroxy groups deriving from glycol split, for example, aldehyde groups, methoxy groups, or oligosaccharide or peptide groups, ranging from a single saccharide or amino acid to more than one unit of length, e.g., 2 or 3 units.

In some embodiments, fewer than 50% of the uronic acid residues are glycol split uronic acid residues (e.g., less than 40%, 30%, 25%, or 20% of the uronic acid residues are glycol split uronic acid residues).

Reducing End Structures

In some instances, at least about 50% of the chains in a polysaccharide preparation described herein have a modified reducing end structure such as a 2,5-anhydromannose residue or a 2,5-anhydromannose that has been reduced to form an alcohol. In some embodiments, at least about 55%, 60%, 65%, 70%, 75%, 80%, 85%, 90%, or 95% of the chains in the preparation have a modified reducing end structure, such that the reducing end includes a 2,5-anhydromannose residue or a 2,5-anhydromannose that has been reduced to form an alcohol.

Polydispersity

The polydispersity of polysaccharide preparations provided herein is about 2 or less, e.g., 1.7 or less, e.g., about 1.7 or 1.6 to 1.2, about 1.4-1.5, and numbers in between.

The term "polydisperse" or "polydispersity" refers to the weight average molecular weight of a composition (Mw) divided by the number average molecular weight (Mn). The number average molecular weight (Mn) is calculated from the following equation: $Mn=\Sigma ci/(\Sigma ci/mi)$. The variable ci is the concentration of the polysaccharide in slice i and Mi is the molecular weight of the polysaccharide in slice i. The summations are taken over a chromatographic peak, which contains many slices of data. A slice of data can be pictured as a vertical line on a plot of chromatographic peak versus time. The elution peak can therefore be divided into many slices. The number average molecular weight is a calculation dependent on the molecular weight and concentration at each slice of data. Methods of determining weight average molecular weight are described above, and were used to determine polydispersity as well.

Methods of Making Polysaccharide Preparations

Various methods of making polysaccharide preparations, e.g., a preparation described herein, are also contemplated. One method includes providing a precursor heparin preparation having a weight average molecular weight of greater than 7000 Da or a chain length of greater than 7 to 18 disaccharides, and processing the precursor heparin preparation (e.g., by enzymatic or chemical depolymerization, e.g., by nitrous acid depolymerization) to obtain a polysaccharide preparation having a weight average molecular weight of about 3000 to 8000 Da or an average chain length of about 7 to 18 disaccharides. For example, the precursor heparin preparation can be unfractionated heparin.

The precursor heparin preparation can be processed by a method comprising depolymerization (e.g., by nitrous acid treatment, hydrolysis, or enzymatic depolymerization) followed by a glycol split reaction. Nitrous acid depolymerization can be accomplished, e.g., by treating the precursor heparin preparation (e.g., UFH) with nitrous acid (e.g., about 0.02 to 0.04 M nitrous acid) at a pH of about 2 to 4 for a specified period of time (e.g., about 1 to 5 hours) at a temperature of about 10 to 30° C. The glycol split reaction involves periodate oxidation using periodate (e.g., about 0.05 M to 0.2 M sodium periodate) for about 10 to 20 hours at a temperature of about 0 to 10° C. In some embodiments, residual impurities such as salts or diethylene glycol (DEG) can be subsequently removed by a chromatographic method, e.g. gel filtration chromatography. Optionally, the oxidized preparation is then reduced by treatment with a reducing agent (e.g., about 0.5 to 2.0% (w/v) sodium borohydride) for about 0.5 to 3 hours at a pH of about 6.0 to 7.0 and a temperature of about 0 to 10° C.

A precursor heparin preparation can be processed using enzymatic digestion, chemical digestion or combinations thereof. Examples of chemical digestion include oxidative depolymerization, e.g., with $H_2O_2$ or $Cu^+$ and $H_2O_2$, deaminative cleavage, e.g., with isoamyl nitrite or nitrous acid, β-eliminative cleavage, e.g., with benzyl ester, and/or by alkaline treatment. Enzymatic digestion can include the use of one or more heparin degrading enzymes. For example, the heparin degrading enzyme(s) can be, e.g., one or more heparanase, heparin lyase, heparan sulfate glycosaminoglycan (HSGAG) lyase, a lyase described as a glycosaminoglycan (GAG) lyase that can also degrade heparin. Preferably, the enzyme cleaves at one or more glycosidic linkages of unsulfated uronic acids.

Biological Activities

The preparations described herein have anti-metastatic activity as assayed in an animal model of metastasis in which B16F10 melanoma cells injected into the tail veins of C57BL/6 mice arrest in the lungs and proliferate as discrete pulmonary foci. This assay is generally described in Gabri et al., 2006, Clin. Cancer Res., 12:7092-98. A preparation may additionally have activity in other experimental models of metastasis, including the C170HM2 assay, in which C170HM2 human colorectal cancer line cells are injected into the peritoneal cavity, where the primary site of metastasis is to the liver. The preparations described herein may also show anti-metastatic activity in spontaneous models of metastasis, such as the AP5LV model, in which AP5LV human colorectal cancer cells are implanted into the peritoneal wall and exhibit spontaneous metastasis to the lung, or the 4T1 model, in which 4T1 murine mammary carcinoma cells implanted in to the mammary fat pad exhibit spontaneous metastasis to the lung and other organs.

The preparations described herein can bind to and/or modulate (e.g., inhibit) an activity of one or more of VEGF, FGF, SDF-1α, HB-EGF, heparanase and P-selectin. In some embodiments, interaction of the preparation with (e.g., binding to) a target protein (e.g., VEGF, FGF, SDF-1α, or P-selectin) can be assayed, e.g., in vitro, e.g., using methods known in the art. Numerous methods and techniques to detect binding or modulation (e.g., inhibition) of activity are known, e.g., standard receptor competition assays, fluorescence energy transfer (FET), fluorescence resonance energy transfer (FRET) (see, for example, U.S. Pat. No. 5,631,169; U.S. Pat. No. 4,868,103), and fluorescence polarization (FP). In some embodiments, evaluating binding of a polysaccharide preparation to a target protein can include a real-time monitoring of the binding interaction, e.g., using Biomolecular Interaction Analysis (BIA) (see, e.g., Sjolander and Urbaniczky (1991) Anal. Chem., 63:2338-2345 and Szabo et al. (1995) Curr. Opin. Struct. Biol., 5:699-705). Surface plasmon resonance or "BIA" detects biospecific interactions in real time, without labeling any of the interactants (e.g., BIAcore).

Activities of VEGF, FGF, and P-selectin on cells in vitro and in vivo are well known in the art. The ability of a polysaccharide preparation to modulate (e.g., inhibit) an activity of VEGF, FGF, or P-selectin can be assayed in vitro or in a cell-based assay or in vivo in an organism. For example, the ability of a polysaccharide preparation to modulate (e.g., inhibit) the activity of VEGF, FGF, or P-selectin to modulate (e.g., stimulate) the proliferation of endothelial cells, e.g., human umbilical vein epithelial cells, can be assayed. Exemplary methods of determining modulation of FGF activity can be found in U.S. Pat. No. 5,733,893. A cell-based assay can be performed using a single cell, or a collection of at least two or more cells. The cell can be a yeast cell (e.g., *Saccharomyces cerevisiae*) or a mammalian cell, e.g., a cell line.

Assays for determining whether a chemotherapeutic agent causes bone marrow derived progenitor cell mobilization can be determined by methods known in the art, see, e.g., Shaked et al. (2008) *Cancer Cell* 14:263-273, which is incorporated herein by reference, and described in the Examples.

Pharmaceutical Compositions

Compositions, e.g., pharmaceutically acceptable compositions, which include a preparation described herein, formulated together with a pharmaceutically acceptable carrier, are provided.

As used herein, "pharmaceutically acceptable carrier" includes any and all solvents, dispersion media, isotonic and absorption delaying agents, and the like that are physiologically compatible with parenteral administration. The carrier can be suitable for any parenteral administration, e.g., intravenous, intramuscular, subcutaneous, intraocular, intraperitoneal, rectal, inhaled or spinal administration (e.g., by injection or infusion).

The compositions of this invention may be in a variety of forms. These include, for example, liquid, semi-solid and solid dosage forms, such as liquid solutions (e.g., injectable and infusible solutions), dispersions or suspensions, and liposomes. The preferred form depends on the intended mode of administration and therapeutic application. Typical preferred compositions are in the form of injectable or infusible solutions. The preferred mode of administration is parenteral (e.g., intravenous, subcutaneous, intraocular, intraperitoneal, intramuscular). In a preferred embodiment, the preparation is administered by intravenous infusion or injection. In another preferred embodiment, the preparation is administered by intramuscular or subcutaneous injection.

The phrases "parenteral administration" and "administered parenterally" as used herein means modes of administration other than enteral and topical administration, usually by injection, and includes, without limitation, intravenous, intramuscular, subcutaneous, intraarterial, intrathecal, intracapsular, intraorbital, intravitreous, intracardiac, intradermal, intraperitoneal, transtracheal, inhaled, subcutaneous, subcuticular, intraarticular, subcapsular, subarachnoid, intraspinal, epidural and intrasternal injection and infusion.

Therapeutic compositions typically should be sterile and stable under the conditions of manufacture and storage. The composition can be formulated as a solution, microemulsion, dispersion, liposome, or other ordered structure suitable to high concentration. Sterile injectable solutions can be prepared by incorporating the active compound (i.e., polysaccharide preparation) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the preferred methods of preparation are vacuum drying and freeze-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, various polymers, monostearate salts and gelatin.

For many therapeutic applications, the preferred route/mode of administration is intravenous injection or infusion. As will be appreciated by the skilled artisan, the route and/or mode of administration will vary depending upon the desired results.

Formulations for injection may be presented in unit dosage form, e.g., in ampoules, syringes, syringe pens, or in multi-dose containers, e.g., with an added preservative. The compositions may take such forms as suspensions, solutions or emulsions in oily or aqueous vehicles, and may contain formulatory agents such as suspending, stabilizing and/or dispersing agents.

For administration by inhalation, the preparation may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Capsules and cartridges of, e.g., gelatin for use in an inhaler or insufflator may be formulated containing a powder mix of the compound and a suitable powder base such as lactose or starch. In addition, dry powder formations for inhalation therapy are within the scope of the invention. Such dry powder formulations may be prepared as disclosed, e.g., in WO 02/32406.

In addition to the compositions described previously, the compounds may also be formulated as a depot preparation. Such long-acting formulations may be formulated with suitable polymeric or hydrophobic materials (for example, as an emulsion in an acceptable oil) or ion exchange resins, or as sparingly soluble derivatives, for example, as a sparingly soluble salt.

The pharmaceutical compositions also may comprise suitable solid or gel phase carriers or excipients. The compositions can be included in a container, pack, or dispenser together with instructions for administration.

The preparation can also be administered with short or long term implantation devices, e.g., a stent. The preparation can be implanted subcutaneously, can be implanted into tissues or organs (e.g., the coronary artery, carotid artery, renal artery and other peripheral arteries, veins, kidney, heart cornea, vitreous, cerebrum, etc.), or can be implanted in physiological spaces around tissues and organs (e.g., kidney capsule, pericardium, thoracic or peritoneal space).

The preparation can also be used to coat various medical devices. For example, the preparation can be used to coat a stent or extracorporeal circuit. Such formulations of the preparations may include using, e.g., controlled release beads, gel or microspheres as well as various polymers such as PLGA, cellulose, alginate or other polysaccharides.

Dosage regimens are adjusted to provide the optimum desired response (e.g., a therapeutic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

It is to be noted that dosage values may vary with the type and severity of the condition to be alleviated. It is to be further understood that for any particular subject, specific dosage regimens should be adjusted over time according to the individual need and the professional judgment of the person administering or supervising the administration of the compositions.

The pharmaceutical compositions of the invention may include a therapeutically effective amount of a preparation. A therapeutically effective amount of the preparation may vary according to factors such as the disease state, age, sex, and weight of the individual and can include more than one unit dose. A therapeutically effective amount is also one in which any toxic or detrimental effects of the preparation are outweighed by the therapeutically beneficial effects. A therapeutically effective amount may inhibit a measurable parameter, e.g., VEGF activity, FGF activity, P-selectin activity, heparanase activity, or size or rate of growth of metastatic lesions, e.g., by at least about 20%, more preferably by at least about 25%, 30%, 40%, even more preferably by at least about 50%, 60%, and still more preferably by at least about 70%, 80% relative to untreated subjects. The ability of a compound to inhibit a measurable parameter, e.g., metastasis or angiogenesis, can be evaluated in an animal model system or in a human (e.g., in a pre-clinical model or a clinical trial). Alternatively, a property of a composition can be evaluated by examining the activity of the compound in an in vitro assay. Exemplary doses for intravenous or subcutaneous administration of the polysaccharide preparation are about 0.03 mg/kg to 0.45 mg/kg, e.g., 0.03 mg/kg, 0.05 mg/kg, 0.1 mg/kg, 0.15 mg/kg, 0.2 mg/kg, 0.22 mg/kg, 0.25 mg/kg, 0.27 mg/kg, 0.3 mg/kg, 0.35 mg/kg, 0.37 mg/kg, 0.4 mg/kg, 0.44 mg/kg, preferably about 0.1 mg/kg, 0.15 mg/kg, 0.2 mg/kg, 0.25 mg/kg, 0.3 mg/kg, 0.35 mg/kg, 0.4 mg/kg, 0.44 mg/kg, 0.47 mg/kg, 0.5 mg/kg, 0.55 mg/kg, 0.60 mg/kg, 0.7 mg/kg, preferably about 0.30 to 0.50 mg/kg, e.g., 0.30 mg/kg, 0.35 mg/kg, 0.40 mg/kg, 0.42 mg/kg, 0.44 mg/kg, 0.47 mg/kg or 0.50 mg/kg. In some embodiments, the polysaccharide preparation can be administered at a dose between 0.5-80 mg/kg, between 0.5-40 mg/kg, between 0.5-30 mg/kg, e.g., between 5-50 mg/kg/day.

Kits

Also within the scope of the invention are a kit comprising a polysaccharide preparation described herein, e.g., a polysaccharide preparation described herein that lacks substantial anticoagulation activity, and a chemotherapeutic agent that is associated with bone marrow derived progenitor cell mobilization; a kit comprising a polysaccharide preparation described herein, e.g., a polysaccharide preparation that lacks substantial anticoagulation activity, and instructions to administer the polysaccharide preparation to a subject with cancer who has been or will be treated with a chemotherapeutic agent that is associated with bone marrow derived progenitor cell mobilization; a kit comprising a polysaccharide preparation described herein, e.g., a polysaccharide preparation that lacks substantial anticoagulation activity, and instructions to administer the polysaccharide preparation to a subject with cancer who has been or will be treated with a chemotherapeutic agent at a dose and/or dosing schedule that is associated with bone marrow derived progenitor cell mobilization, e.g., a dose and/or dosing schedule described herein; a kit comprising a chemotherapeutic agent that is associated with bone marrow derived progenitor cell mobilization, and instructions to administer the chemotherapeutic agent to a subject in combination with a polysaccharide preparation described herein, e.g., a polysaccharide preparation described herein that lacks substantial anticoagulant activity; or a kit comprising a chemotherapeutic agent, and instructions to administer the chemotherapeutic agent to a subject at a dose and/or dosing schedule associated that is associated with bone marrow progenitor cell mobilization and instructions to administer the chemotherapeutic agent in combination with a polysaccharide preparation described herein, e.g., a polysaccharide preparation described herein that lacks substantial anticoagulant activity.

The kit can include one or more other elements including: other reagents, e.g., a therapeutic agent; devices or other materials for preparing the polysaccharide preparation for administration; pharmaceutically acceptable carriers; and devices or other materials for administration to a subject. The instructions can include instructions for therapeutic application including suggested dosages and/or modes of administration, e.g., in a patient having a disorder, e.g., a disorder described herein. The kit can further contain at least one additional reagent, such as a diagnostic or therapeutic agent, e.g., a diagnostic or therapeutic agent as described herein, formulated as appropriate, in one or more separate pharmaceutical preparations.

Uses

The polysaccharide preparations can be used to treat a subject. As used herein, a subject is a mammal, e.g., a non-human experimental mammal, a veterinary mammal, or a human. Non-human mammals include a primate, cow, horse, pig, sheep, goat, dog, cat, or rodent.

The preparations provided herein can be used, for example, to treat or prevent a metastatic disorder (e.g., a cancer, e.g., a carcinoma or other solid or hematological cancer). As used herein, the term "cancer" is meant to include all types of cancerous growths or oncogenic processes, metastatic tissues or malignantly transformed cells, tissues, or organs, irrespective of histopathologic type or stage of invasiveness. Methods and compositions disclosed herein are particularly useful for treating, or reducing the size, numbers, or rate of growth of, metastatic lesions associated with cancer.

Examples of cancers include, but are not limited to, solid tumors, soft tissue tumors, hematopoietic tumors and metastatic lesions. Examples of solid tumors include malignancies, e.g., sarcomas, adenocarcinomas, and carcinomas, of the various organ systems, such as those affecting head and neck (including pharynx), thyroid, lung (small cell or non small cell lung carcinoma), breast, lymphoid, gastrointestinal (e.g., oral, esophageal, stomach, liver, pancreas, small intestine, colon and rectum, anal canal), genitals and genitourinary tract (e.g., renal, urothelial, bladder, ovarian, uterine, cervical, endometrial, prostate, testicular), CNS (e.g., neural or glial cells, e.g., neorublastoma or glioma), skin (e.g., melanoma). Examples of hematopoietic cancers that can be treated include hemangiomas, multiple myeloma, lymphomas and leukemias and myelodysplasia. Methods and compositions disclosed herein are particularly useful for treating, e.g., reducing or delaying, metastatic lesions associated with the aforementioned cancers. In some embodiments, the patient will have undergone one or more of surgical removal of a tissue, chemotherapy, or other anti-cancer therapy and the primary or sole target will be metastatic lesions, e.g., metastases in the bone or lymph nodes or lung or liver or peritoneal cavity or the CNS or other organs.

The methods of the invention, e.g., methods of treatment, can further include the step of monitoring the subject, e.g., for a change (e.g., an increase or decrease) in one or more of: tumor size; levels of a cancer marker, for a patient with cancer; the size or rate of appearance of new lesions, e.g., in a scan; the appearance of new disease-related symptoms; the size of soft tissue mass, e.g., a decrease or stabilization; changes in blood flow measured by imaging technology; survival; progression-free survival; quality of life, e.g., amount of disease associated pain, e.g., bone pain; or any other parameter related to clinical outcome. In one embodiment, the subject can be monitored for bone marrow derived progenitor cell mobilization (e.g., EPC, HPC, iMC (MDSC) and/or MPC mobilization). The subject can be monitored in one or more of the following periods: prior to beginning of treatment; during the treatment; or after one or more elements of the treatment have been administered. Monitoring can be used to evaluate the need for further treatment with the same preparation or for additional treatment with additional agents. Generally, a decrease in one or more of the parameters described above is indicative of the improved condition of the subject.

The preparations described herein can be administered to a subject in single or multiple doses to treat or prevent a metastatic or cancerous disorder, e.g., a cancerous disorder described herein.

The preparations described herein can also be used to treat inflammatory, autoimmune, fibrotic, fibroproliferative, atopic, or angiogenic disorders. Examples of inflammatory disorders include but are not limited to chronic obstructive pulmonary disease, asthma, rheumatoid arthritis, inflammatory bowel disease (including Crohns disease and ulcerative colitis), multiple sclerosis, psoriasis, ischemia-reperfusion injuries, septic shock, age-related macular degeneration (e.g., wet age-related macular degeneration), atherosclerosis, Alzheimer's disease, Parkinson's disease, cardiovascular disease, vasculitis, type I and II diabetes, metabolic syndrome, diabetic retinopathy, restenosis. Examples of autoimmune diseases include but are not limited to asthma, rheumatoid arthritis, inflammatory bowel disease, multiple sclerosis, psoriasis, type I diabetes, systemic lupus erythematosus (SLE), Sjögren's syndrome, Hashimoto's thyroiditis, Graves' disease, Guillain-Barrú syndrome, autoimmune hepatitis, Myasthenia gravis. Examples of fibrotic diseases include but are not limited to scleroderma, liver fibrosis, pancreatic fibrosis, chronic obstructive pulmonary disease, diabetic nephropathy, sarcoidosis, idiopathic pulmonary fibrosis, cirrhosis, cystic fibrosis, neurofibromatosis, endometriosis, post-operative fibroids, restenosis. Examples of atopic disease include but are not limited to atopic dermatitis, atopic asthma, and allergic rhinitis.

Examples of fibroproliferative disorders include systemic and local scleroderma, keloids and hypertrophic scars, atherosclerosis, restenosis, fibrosarcoma, neurofibromatosis, and rheumatoid arthritis. Examples of scarring associated with trauma include scarring due to surgery, chemotherapeutic-induced fibrosis, radiation-induced fibrosis, scarring associated with injury or burns.

In one embodiment, the polysaccharide preparations are used for inhibiting angiogenesis, e.g., to treat angiogenic disorders. Angiogenesis as used herein is the inappropriate formation of new blood vessels. Angiogenic disorders include, but are not limited to, tumors, neovascular disorders of the eye, endometriosis, macular degeneration, osteoporosis, psoriasis, arthritis, cancer, hemangiomas, and cardiovascular disorders. It is understood that some disorders will fall within more than one category of disease described herein.

The preparations described herein can also be used to treat or prevent infectious disorders such as, e.g., malaria.

Combination Therapy

The methods and compositions of the invention can be used in combination with other therapeutic modalities. Administered "in combination", as used herein, means that two (or more) different treatments are delivered to the subject during the course of the subject's affliction with the disorder, such that the effects of the treatments on the patient overlap at a point in time. In some embodiments, the delivery of one treatment is still occurring when the delivery of the second begins, so that there is overlap in terms of administration. This is sometimes referred to herein as "simultaneous" or "concurrent delivery." In other embodiments, the delivery of one treatment ends before the delivery of the other treatment begins. In some embodiments of either case, the treatment is more effective because of combined administration. For example, the second treatment is more effective, e.g., an equivalent effect is seen with less of the second treatment, or the second treatment reduces symptoms to a greater extent, than would be seen if the second treatment were administered in the absence of the first treatment, or the analogous situation is seen with the first treatment. In some embodiments, delivery is such that the reduction in a symptom, or other parameter related to the disorder is greater than what would be observed with one treatment delivered in the absence of the other. The effect of the two treatments can be partially additive, wholly additive, or greater than additive. The delivery can be such that an effect of the first treatment delivered is still detectable when the second is delivered.

In one embodiment, the methods of the invention include administering to the subject a preparation described herein, in combination with one or more additional therapies, e.g., surgery, radiation therapy, or administration of another therapeutic preparation. In one embodiment, the additional therapy may include chemotherapy, e.g., a cytotoxic agent. In one embodiment the additional therapy may include a targeted therapy, e.g. a tyrosine kinase inhibitor, a proteasome inhibitor, a protease inhibitor. In one embodiment, the additional therapy may include an anti-inflammatory, anti-angiogenic, anti-fibrotic, or anti-proliferative compound, e.g., a steroid, a biologic immunomodulator, a monoclonal antibody, an antibody fragment, an aptamer, an siRNA, an antisense molecule, a fusion protein, a cytokine, a cytokine receptor, a bronchodialator, a statin, an anti-inflammatory agent (e.g. methotrexate), an NSAID. In another embodiment, the additional therapy could include combining therapeutics of different classes. The polysaccharide preparation and the additional therapy can be administered simultaneously or sequentially.

Exemplary cytotoxic agents that can be administered in combination with the polysaccharide preparation include antimicrotubule agents, topoisomerase inhibitors, antimetabolites, protein synthesis and degradation inhibitors, mitotic inhibitors, alkylating agents, platinating agents, inhibitors of nucleic acid synthesis, histone deacetylase and DNA methyltransferase inhibitors, nitrogen mustards, nitrosoureas, ethylenimines, alkyl sulfonates, triazenes, folate analogs, nucleoside analogs, ribonucleotide reductase inhibitors, vinca alkaloids, taxanes, epothilones, intercalating agents, agents capable of interfering with a signal transduction pathway, agents that promote apoptosis and radiation, antibody conjugates that bind surface proteins to deliver a toxic agent. In one embodiment, the cytotoxic agent that can be administered with a preparation described herein is a platinum-based agent (such as cisplatin), cyclophosphamide, dacarbazine, methotrexate, fluorouracil, gemcitabine, capecitabine, hydroxyurea, topotecan, irinotecan, azacytidine, vorinostat, ixabepilone, bortezomib, taxanes (paclitaxel, docetaxel), cytochalasin B, gramicidin D, ethidium bromide, emetine, mitomycin, etoposide, tenoposide, vincristine, vinblastine, vinorelbine, colchicin, anthracyclines (doxorubicin, epirubicin, daunorubicin), dihydroxy anthracin dione, mitoxantrone, mithramycin, actinomycin D, adriamycin, 1-dehydrotestosterone, glucocorticoids, procaine, tetracaine, lidocaine, propranolol, puromycin, ricin, and maytansinoids.

The combination therapy can also include a composition of the present invention coformulated with, and/or coadministered with, one or more additional therapeutic agents, e.g., one or more anti-cancer agents, cytotoxic or cytostatic agents, hormone treatment, small molecule inhibitors of receptor tyrosine kinases and other tyrosine kinases including HER-2, EGFR, VEGFR, BCR-ABL, c-KIT (such as Gefitinib, Erlotinib, Lapatinib, Sorafenib, Sunitinib, Imatinib, Dasatinib, Nilotinib) or mTOR (such as temsirolimus, everolimus, rapamycin), or cytokines or chemokines, vaccines, antibodies against cell membrane receptors pathways including EGF-EGFR, VEGF-VEGFR, CD19, CD20, CD3, CTLA-4 (such as Trastuzumab, Cetuximab, Panitumumab, Bevacizumab, Rituximab, Tositumomab) and/or other immunotherapies.

Anti-Angiogenic Agent or Tyrosine Kinase Inhibitors

The polysaccharide preparations described herein can be administered in combination with an anti-angiogenic agent or tyrosine kinase inhibitor to treat a subject having cancer, e.g., a primary tumor, or having or at risk of having metastasis of a primary tumor. As discussed herein, administration of anti-angiogenic agents and tyrosine kinase inhibitors to a subject having cancer is associated with mobilization of bone marrow derived progenitor cells such as endothelial progenitor cells.

In one embodiment, the anti-angiogenic agent or tyrosine kinase inhibitor is administered in an amount and/or dosing schedule that is associated with (e.g., causes or results in) bone marrow derived progenitor cell mobilization. For example, the anti-angiogenic agent or tyrosine kinase inhibitor is administered in an amount and/or dosing schedule that is associated with (e.g., causes or results in) endothelial progenitor cell mobilization. The dose and/or dosing schedule can be a dose and/or dosing schedule described herein.

In one embodiment, the anti-angiogenic agent or tyrosine kinase inhibitor is selected from the group consisting of: an epidermal growth factor (EGF) pathway inhibitor (e.g., an epidermal growth factor receptor (EGFR) inhibitor), a vascular endothelial growth factor (VEGF) pathway inhibitor (e.g., a vascular endothelial growth factor receptor (VEGFR) inhibitor (e.g., a VEGFR-1 inhibitor, a VEGFR-2 inhibitor, a VEGFR-3 inhibitor)), a platelet derived growth factor (PDGF) pathway inhibitor (e.g., a platelet derived growth factor receptor (PDGFR) inhibitor (e.g., a PDGFR-β inhibitor)), a TGF pathway inhibitor, a KIT pathway inhibitor, a RAF-1 inhibitor and a RET inhibitor. In some embodiments, the subject has been treated or will be treated with an anti-angiogenic agent or a tyrosine kinase inhibitor selected from the group consisting of: bevacizumab (Avastin®), ranibizumab (Lucentis®), imatinib (Gleevec®), cetuximab (Erbitux®), sunitinib (Sutent®), sorafenib (Nexavar®), tivozanib (AV-951), cediranib (AZD2171), dasatinib (Sprycel®), nilotinib (AMN-107), CP-547632, erlotinib (Tarceva®), panitumumab (Vectibix®), pazopanib (Votrient®), axitinib and gefitinib (Iressa®).

A PDGF pathway inhibitor includes, without limitation, tyrphostin AG 1296, tyrphostin 9, 1,3-butadiene-1,1,3-tricarbonitrile, 2-amino-4-(1H-indol-5-yl)-(9C1), imatinib (Gleevec®) and gefitinib (Iressa®) and those compounds generically and specifically disclosed in European Patent No.: 0 564 409 and PCT Publication No.: WO 99/03854.

A VEGF pathway inhibitor includes, without limitation, anti-VEGF antibodies, e.g., bevacizumab (Avastin®), and small molecules, e.g., sunitinib (Sutent®), sorafinib (Nexavar®), ZD6474 (also known as vandetanib) (Zactima™), SU6668, CP-547632 and AZD2171 (also known as cediranib) (Recentin™).

A EGF pathway inhibitor includes, without limitation, anti-EGFR antibodies, e.g., cetuximab (Erbitux®), panitumumab (Vectibix®), and gefitinib (Iressa®), and small molecules such as tyrphostin 46, EKB-569, erlotinib (Tarceva®), gefitinib (Iressa®), lapatinib (Tykerb®) and those compounds that are generically and specifically disclosed in WO 97/02266, EP 0 564 409, WO 99/03854, EP 0 520 722, EP 0 566 226, EP 0 787 722, EP 0 837 063, U.S. Pat. No. 5,747, 498, WO 98/10767, WO 97/30034, WO 97/49688, WO 97/38983 and WO 96/33980.

In one embodiment, the cancer is gastrointestinal cancer. The gastrointestinal cancer can be a chemotherapeutic refractory, a chemotherapeutic resistant, and/or a relapsed cancer, e.g., the gastrointestinal cancer is refractory to imatinib mesylate, resistant to imatinib mesylate or relapsed after treatment with imatinib mesylate.

In an embodiment, the cancer is renal cell cancer, e.g., advanced or metastatic renal cell carcinoma, e.g., a chemotherapeutic refractory, a chemotherapeutic resistant, and/or a relapsed carcinoma, e.g., the renal cell carcinoma is refractory to a cytokine (e.g., interleukin-2 or interferon), resistant to a cytokine (e.g., interleukin-2 or interferon) or relapsed after treatment with a cytokine (e.g., interleukin-2 or interferon). In some embodiments, a renal cell cancer is treated according to methods described herein with pazopanib (Votrient®) (e.g., at a dose of 800 mg or less (e.g., 600 mg, 400 mg, 200 mg) daily, or sorafenib (Nexavar®) in combination with a polysaccharide preparation described herein. In some embodiments, a polysaccharide described herein can be administered in combination with sunitinib. In one embodiment, the sunitinib is administered orally at a dose of 20 mg, 25 mg, 30 mg, 35 mg, 40 mg, 45 mg, 50 mg, 55 mg, 60 mg sunitinib orally, once daily, on a schedule. In one embodiment, the schedule is administration of sunitinib everyday for three, four or five weeks followed by one, two or three weeks of no administration or continuously without 'drug holiday'.

In an embodiment, the cancer is colorectal cancer, e.g., metastatic colorectal cancer, e.g., a chemotherapeutic refractory, a chemotherapeutic resistant, and/or a relapsed cancer. In some embodiments, a colorectal cell cancer is treated with a polysaccharide preparation described herein in combination with bevacizumab (Avastin®) (e.g., at a dose of 5 to 10 mg/kg every 12, 13, 14, 15, 16 days), e.g., in further combination with one or more of a topoisomerase inhibitor (e.g., topotecan, irinotecan, etoposide, teniposide, lamellarin D, camptothecin), a platinum-based agent (e.g., cisplatin, carboplatin, oxaliplatin), an antimetabolite (e.g., 5FU) and leucovorin.

In an embodiment, the cancer is lung cancer, e.g., small cell lung cancer or non-small cell lung cancer, e.g., a chemotherapeutic refractory, a chemotherapeutic resistant, and/or a relapsed cancer. In some embodiments, the lung cell cancer is treated with a polysaccharide preparation described herein in combination with bevacizumab (Avastin®) (e.g., at a dose of 5 to 10 mg/kg every 12, 13, 14, 15, 16 days), e.g., in further combination with one or more of a topoisomerase inhibitor (e.g., topotecan, irinotecan, etoposide, teniposide, lamellarin D, camptothecin), a platinum-based agent (e.g., cisplatin, carboplatin, oxaliplatin), an antimetabolite (e.g., 5FU) and leucovorin.

In an embodiment, the cancer is breast cancer, e.g., metastatic breast cancer, e.g., a chemotherapeutic refractory, a chemotherapeutic resistant, and/or a relapsed breast cancer. The breast cancer can be estrogen receptor positive breast cancer; estrogen receptor negative breast cancer; HER-2 positive breast cancer; HER-2 negative breast cancer; progesterone receptor positive breast cancer; progesterone receptor negative breast cancer; estrogen receptor negative, HER-2 negative and progesterone receptor negative breast cancer (i.e., triple negative breast cancer). In some embodiments, the breast cancer is treated with a polysaccharide preparation described herein in combination with bevacizumab (Avastin®) (e.g., at a dose of 5 to 10 mg/kg every 12, 13, 14, 15, 16 days), e.g., in further combination with a taxane (e.g., docetaxel, paclitaxel, larotaxel, cabizitaxel). Also, e.g., in combination with anthracycline (daunorubicin (Daunomycin®), doxorubicin (Adriamycin®)), e.g. in combination with platinum (e.g. cisplatin) e.g., in combination with estrogen inhibitor (e.g. aromatase inhibitors, tamoxifen (Nolvadex®), exemestane (Aromasin®), anastrozole (Arimidex®) and letrozole (Femara®), e.g. in combination with EGF/HER2 inhibitors (e.g. Lapatinib (Tykerb®), trastuzumab (Herceptin®).

In an embodiment, the cancer is a glioblastoma, e.g., a chemotherapeutic refractory, a chemotherapeutic resistant, and/or a relapsed glioblastoma. In certain embodiments, the glioblastoma is treated with a polysaccharide preparation described herein in combination with bevacizumab (Avastin®) (e.g., at a dose of 5 to 10 mg/kg every 12, 13, 14, 15, 16 days).

In one embodiment, the cancer is gastrointestinal cancer and a polysaccharide described herein is administered in combination with sunitinib. In some embodiments, the sunitinib is administered orally at a dose of 20 mg, 25 mg, 30 mg, 35 mg, 40 mg, 45, mg, 50 mg, 55 mg, 60 mg, once daily, on a schedule. In one embodiment, the schedule is administration of sunitinib everyday for three, four or five weeks followed by one, two or three weeks of no administration or continuously without 'drug holiday'.

In an embodiment, the cancer is a leukemia (e.g., chronic myeloid leukemia or acute lymphoblastic leukemia, e.g., Philadelphia chromosome positive chronic myeloid leukemia or acute lymphoblastic leukemia), e.g., a chemotherapeutic refractory, a chemotherapeutic resistant, and/or a relapsed leukemia, e.g., refractory, resistant, and/or relapsed to imatinib. In some embodiments, the leukemia is treated with a polysaccharide preparation described herein in combination with dasatinib (e.g., at a dose of 120 mg/day, 130 mg/day, 140 mg/day, 150 mg/day, e.g., administered twice daily).

In an embodiment, the cancer is a pancreatic cancer (e.g., advanced pancreatic cancer). In some embodiments, the pancreatic cancer is treated with a polysaccharide preparation described herein in combination with gemcitabine, erlotinib, Abraxane (a taxol conjugate), a mTOR inhibitor, a VEGF inhibitor (e.g., a VEGF inhibitor described herein), a sonic hedgehog inhibitor.

Vascular Disrupting Agents

The polysaccharide preparations described herein can be administered in combination with a vascular disrupting agent to treat a subject having cancer, e.g., a primary tumor, or having or at risk of having metastasis of a primary tumor. The administration of vascular disrupting agents is associated with mobilization of bone marrow derived progenitor cells such as endothelial progenitor cells in subjects having cancer.

In one embodiment, the vascular disrupting agent is administered in an amount and/or dosing schedule that is associated with (e.g., causes or results in) bone marrow derived progenitor cell mobilization. For example, the vascular disrupting agent is administered in an amount and/or dosing schedule that is associated with (e.g., causes or results in) endothelial progenitor cell mobilization. The dose and/or dosing schedule can be a dose and/or dosing schedule described herein.

Exemplary vascular disrupting agents include, but are not limited to, AVE8062, vadimezan, ZD6126, combretastatin A-4 disodium phosphate (CA4P) or Oxi4503, DMXAA (ASA404), NPI-2358.

In one embodiment, the cancer is lung cancer (e.g., small cell lung cancer or non-small cell lung cancer). The lung cancer can be resistant, relapsed or refractory to treatment with a chemotherapeutic agent, e.g., a VEGF pathway inhibitor (e.g., bevacizumab) or an EGF pathway inhibitor. The lung cancer can be locally advanced or metastatic lung cancer. In another embodiment, the cancer is urothelial cancer (e.g., cancer of the bladder, urethra, ureter, renal pelvis), e.g., locally advanced or metastatic urothelial cancer. The urothelial cancer can be resistant, relapsed or refractory to another chemotherapeutic agent, e.g., a platinum based agent (e.g., cisplatin, carboplatin, oxaliplatin) or a pyrimidine analog (e.g., gemcitabine). A polysaccharide described herein can be administered in combination with ASA404, e.g., ASA404 at a dose of 1,600 mg/m$^2$, 1,700 mg/m$^2$, 1,800 mg/m$^2$, 1,900 mg/m$^2$, 2,000 mg/m$^2$ on a schedule. In one embodiment, the schedule is administration of ASA404 every 18, 19 20, 21, 22, 23 or 24 days, e.g., for 4, 5, 6, 7 cycles. The treatment can further include administration of one or more additional chemotherapeutic agent, e.g., a taxane (e.g., docetaxel, paclitaxel, larotaxel, cabizitaxel) or a platinum based agent (e.g., cisplatin, carboplatin, oxaliplatin). In some embodiments, the lung cancer is treated with a polysaccharide preparation described herein in combination with NPI-2358 (e.g., at a dose of 20, 30, 40 mg/m$^2$).

In an embodiment, the cancer is a head and neck cancer (e.g., anaplastic carcinoma of the thyroid), e.g., locally advanced or metastatic head and neck cancer. In another embodiment, the cancer is a glioma. In yet another embodiment, the cancer is lung cancer (e.g., small cell lung cancer or non small cell lung cancer), e.g., locally advanced or metastatic lung cancer. The cancer can be chemotherapeutic refractory, a chemotherapeutic resistant, and/or a relapsed. In certain embodiments, the cancer is treated with a polysaccharide preparation described herein in combination with CA4P (e.g., at a dose of 50 mg/m$^2$, 60 mg/m$^2$, 70 mg/m$^2$ on a schedule. The dosing schedule can be, e.g., administration of CA4P weekly for three weeks then one week without administration.

In an embodiment, the cancer is a sarcoma (e.g., a soft tissue sarcoma), e.g., locally advanced or metastatic sarcoma. The cancer can be chemotherapeutic refractory, a chemotherapeutic resistant, and/or a relapsed to another chemotherapeutic agent, e.g., an anthracycline or an alkylating agent (e.g., ifosfamide). In certain embodiments, the cancer is treated with a polysaccharide preparation described herein in combination with AVE8026 (e.g., at a dose of 15 mg/m$^2$, 20 mg/m$^2$, 25 mg/m$^2$, 30 mg/m$^2$ on a schedule). The dosing schedule can be, e.g., administration of AVE8026 every three weeks. In some embodiments, the treatment can further include administration of one or more additional chemotherapeutic agents, e.g., a platinum based agent (e.g., cisplatin, carboplatin, oxaliplatin) and a taxane (e.g., docetaxel, paclitaxel, larotaxel, cabizitaxel).

Taxanes

The polysaccharide preparations described herein can be administered in combination with a taxane to treat a subject having cancer, e.g., a primary tumor, or having or at risk of having metastasis of a primary tumor. As discussed herein, administration of a taxane to a subject having cancer is associated with mobilization of bone marrow derived progenitor cells such as endothelial progenitor cells.

In one embodiment, the taxane is administered in an amount and/or dosing schedule that is associated with (e.g., causes or results in) bone marrow derived progenitor cell mobilization. For example, the taxane is administered in an amount and/or dosing schedule that is associated with (e.g., causes or results in) endothelial progenitor cell mobilization. The dose and/or dosing schedule can be a dose and/or dosing schedule described herein.

In one embodiment, the cancer is breast cancer (e.g., locally advanced or metastatic breast cancer). The breast cancer can be estrogen receptor positive breast cancer; estrogen receptor negative breast cancer; HER-2 positive breast cancer; HER-2 negative breast cancer; progesterone receptor positive breast cancer; progesterone receptor negative breast cancer; estrogen receptor negative, HER-2 negative and progesterone receptor negative breast cancer (i.e., triple negative breast cancer). The breast cancer can be resistant, relapsed or refractory to treatment with a chemotherapeutic agent, e.g., an alkylating agent (e.g., cyclophosphamide, dacarbazine, melphalan, ifosfamide, temozolomide) or an anthracycline (e.g., daunorubicin, doxorubicin, epirubicin, valrubicin and idarubicin). In some embodiments, a polysaccharide described herein can be administered in combination with docetaxel, e.g., docetaxel at a dose of 60 mg/m$^2$, 70 mg/m$^2$, 75 mg/m$^2$, 80 mg/m$^2$, 90 mg/m$^2$, 100 mg/m$^2$, 105 mg/m$^2$, 110 mg/m$^2$, 115 mg/m$^2$ on a schedule. In one embodiment, the schedule is administration of docetaxel every three weeks. In another embodiment, a polysaccharide described herein can be administered in combination with paclitaxel, e.g., paclitaxel at a dose of 125 mg/m$^2$, 135 mg/m$^2$, 145 mg/m$^2$, e.g., infused over about 2, 3, or 4 hours, or 165 mg/m$^2$, 175 mg/m$^2$, 185 mg/m$^2$, 195 mg/m$^2$, e.g., infused over about 22, 23, 24 or 25 hours, on a schedule. In one embodiment, the schedule is administration of paclitaxel every three weeks. The treatment can further include administration of one or more additional chemotherapeutic agent, e.g., a vinca alkaloid (e.g., vinblastine, vincristine, vindesine, vinorelbine) or an anthracycline (e.g., daunorubicin, doxorubicin, epirubicin, valrubicin and idarubicin, or a platinum based agent (e.g. cisplatin).

In another embodiment, the cancer is lung cancer (e.g., small cell lung cancer or non small cell lung cancer), e.g., locally advanced or metastatic lung cancer. The lung cancer can be resistant, relapsed or refractory to a chemotherapeutic agent, e.g., a platinum based agent (e.g., cisplatin, carboplatin, oxaliplatin). A polysaccharide described herein can be administered in combination with docetaxel, e.g., docetaxel at a dose of 60 mg/m$^2$, 70 mg/m$^2$, 75 mg/m$^2$, 80 mg/m$^2$, 90 mg/m$^2$, 100 mg/m$^2$, 105 mg/m$^2$, 110 mg/m$^2$, 115 mg/m$^2$ on a schedule. In one embodiment, the schedule is administration of docetaxel every three weeks. In another embodiment, a polysaccharide described herein can be administered in combination with paclitaxel, e.g., paclitaxel at a dose of 125 mg/m$^2$, 135 mg/m$^2$, 145 mg/m$^2$, e.g., infused over about 2, 3, or 4 hours, or 165 mg/m$^2$, 175 mg/m$^2$, 185 mg/m$^2$, 195 mg/m$^2$, e.g., infused over about 22, 23, 24 or 25 hours, on a schedule. In one embodiment, the schedule is administration of paclitaxel every three weeks. The treatment can further include administration of one or more additional chemotherapeutic agent, e.g., a vinca alkaloid (e.g., vinblastine, vincristine, vindesine, vinorelbine) or an alkylating agent (e.g., cyclophosphamide, dacarbazine, melphalan, ifosfamide, temozolomide).

In one embodiment, the cancer is prostate cancer (e.g., locally advanced or metastatic prostate cancer). The prostate cancer can be resistant, relapsed or refractory to treatment with a chemotherapeutic agent. A polysaccharide described herein can be administered in combination with docetaxel, e.g., docetaxel at a dose of 60 mg /m$^2$, 70 mg/m$^2$, 75 mg/m$^2$, 80 mg/m$^2$, 90 mg/m$^2$, 100 mg/m$^2$, 105 mg/m$^2$, 110 mg/m$^2$, 115 mg/m$^2$ on a schedule. In one embodiment, the schedule is administration of docetaxel every three weeks. In another embodiment, a polysaccharide described herein can be administered in combination with docetaxel, e.g., docetaxel at a dose of 20 mg/m$^2$, 25 mg/m$^2$, 30 mg/m$^2$, 35 mg/m$^2$, 40 mg/m$^2$ on a schedule. In one embodiment, the schedule is weekly administration of docetaxel. The treatment can further include administration of one or more additional chemotherapeutic agent.

In one embodiment, the cancer is ovarian cancer (e.g., locally advanced or metastatic ovarian cancer). The ovarian cancer can be resistant, relapsed or refractory to treatment with a chemotherapeutic agent, e.g., a platinum based agent (e.g., cisplatin, carboplatin, oxaliplatin). A polysaccharide described herein can be administered in combination with paclitaxel, e.g., paclitaxel at a dose of 125 mg/m$^2$, 135 mg/m$^2$, 145 mg/m$^2$, e.g., infused over about 2, 3, or 4 hours, or 165 mg/m$^2$, 175 mg/m$^2$, 185 mg/m$^2$, 195 mg/m$^2$, e.g., infused over about 22, 23, 24 or 25 hours, on a schedule. In one embodiment, the schedule is administration of paclitaxel every three weeks. The treatment can further include administration of one or more additional chemotherapeutic agent.

In one embodiment, the cancer is a sarcoma (e.g., AIDS-related Kaposi sarcoma), e.g., locally advanced or metastatic sarcoma). The sarcoma can be resistant, relapsed or refractory to treatment with a chemotherapeutic agent, e.g., an anthracycline (e.g., daunorubicin, doxorubicin, epirubicin, valrubicin and idarubicin). A polysaccharide described herein can be administered in combination with paclitaxel, e.g., paclitaxel at a dose of 125 mg/m$^2$, 135 mg/m$^2$, 145 mg/m$^2$, e.g., infused over about 2, 3, or 4 hours, or 155 mg/m$^2$, 165 mg/m$^2$, 175 mg/m$^2$, 185 mg/m$^2$, 195 mg/m$^2$, e.g., infused over about 22, 23, 24 or 25 hours, on a schedule. In one embodiment, the schedule is administration of paclitaxel every three weeks. The treatment can further include administration of one or more additional chemotherapeutic agent.

Pyrimidine Analogues

The polysaccharide preparations described herein can be administered in combination with a pyrimidine analogue (e.g., fluorouracil) to treat a subject having cancer, e.g., a primary tumor, or having or at risk of having metastasis of a primary tumor. The administration of pyrimidine analogues such as fluorouracil can be associated with mobilization of bone marrow derived progenitor cells such as endothelial progenitor cells in subjects having cancer.

In one embodiment, the pyrimidine analogue (e.g., fluorouracil) is administered in an amount and/or dosing schedule that is associated with (e.g., causes or results in) bone marrow derived progenitor cell mobilization. For example, the vascular disrupting agent is administered in an amount and/or dosing schedule that is associated with (e.g., causes or results in) endothelial progenitor cell mobilization. The dose and/or dosing schedule can be a dose and/or dosing schedule described herein.

In one embodiment, the cancer is breast cancer (e.g., locally advanced or metastatic breast cancer). The breast cancer can be estrogen receptor positive breast cancer; estrogen receptor negative breast cancer; HER-2 positive breast cancer; HER-2 negative breast cancer; progesterone receptor positive breast cancer; progesterone receptor negative breast cancer; estrogen receptor negative, HER-2 negative and progesterone receptor negative breast cancer (i.e., triple negative breast cancer). The breast cancer can be resistant, relapsed or refractory to treatment with a chemotherapeutic agent, e.g., an alkylating agent (e.g., cyclophosphamide, dacarbazine, melphalan, ifosfamide, temozolomide), an anthracycline (e.g., daunorubicin, doxorubicin, epirubicin, valrubicin and idarubicin), a taxane (e.g., docetaxel or paclitaxel) or a platinum based agent (e.g. cisplatin). In some embodiments, a polysaccharide described herein can be administered in combination with fluorouracil, e.g., fluorouracil at a dose of 8 mg/m$^2$, 10 mg/m$^2$, 12 mg/m$^2$, 14 mg/m$^2$, 16 mg/m$^2$ on a schedule. In one embodiment, the schedule is administration of fluorouracil once daily for four days, and then, e.g., at a reduced dose on day 6, 8, 10 and 12. The treatment can further include administration of one or more additional chemotherapeutic agent, e.g., an alkylating agent (e.g., cyclophosphamide, dacarbazine, melphalan, ifosfamide, temozolomide), an anthracycline (e.g., daunorubicin, doxorubicin, epirubicin, valrubicin and idarubicin), or a taxane (e.g., docetaxel or paclitaxel). The treatment can further include administration of leucovorin.

In one embodiment, the cancer is colorectal cancer (e.g., locally advanced or metastatic colorectal cancer). The colorectal cancer can be resistant, relapsed or refractory to treatment with a chemotherapeutic agent. In some embodiments, a polysaccharide described herein can be administered in combination with fluorouracil, e.g., fluorouracil at a dose of 8 mg/m$^2$, 10 mg/m$^2$, 12 mg/m$^2$, 14 mg/m$^2$, 16 mg/m$^2$ on a schedule. In one embodiment, the schedule is administration of fluorouracil once daily for four days, and then, e.g., at a reduced dose on day 6, 8, 10 and 12. The treatment can further include administration of one or more additional chemotherapeutic agent, e.g., an alkylating agent (e.g., cyclophosphamide, dacarbazine, melphalan, ifosfamide, temozolomide), an anthracycline (e.g., daunorubicin, doxorubicin, epirubicin, valrubicin and idarubicin), or a taxane (e.g., docetaxel, paclitaxel, larotaxel, cabizitaxel). The treatment can further include administration of leucovorin.

In one embodiment, the cancer is gastric cancer (e.g., locally advanced or metastatic gastric cancer). The gastric cancer can be resistant, relapsed or refractory to treatment with a chemotherapeutic agent. In some embodiments, a polysaccharide described herein can be administered in combination with fluorouracil, e.g., fluorouracil at a dose of 8 mg/m$^2$, 10 mg/m$^2$, 12 mg/m$^2$, 14 mg/m$^2$, 16 mg/m$^2$ on a schedule. In one embodiment, the schedule is administration of fluorouracil once daily for four days, and then, e.g., at a reduced dose on day 6, 8, 10 and 12. The treatment can further include administration of one or more additional chemotherapeutic agent, e.g., a platinum based agent (e.g., cisplatin, carboplatin, oxaliplatin), a taxane (docetaxel, paclitaxel, larotaxel, cabizitaxel) and an anthracycline (e.g., daunorubicin, doxorubicin, epirubicin, valrubicin and idarubicin). The treatment can further include administration of leucovorin.

In one embodiment, the cancer is pancreatic cancer (e.g., locally advanced or metastatic pancreatic cancer). The pancreatic cancer can be resistant, relapsed or refractory to treatment with a chemotherapeutic agent. In some embodiments, a polysaccharide described herein can be administered in combination with fluorouracil, e.g., fluorouracil at a dose of 8 mg/m$^2$, 10 mg/m$^2$, 12 mg/m$^2$, 14 mg/m$^2$, 16 mg/m$^2$ on a schedule. In one embodiment, the schedule is administration of fluorouracil once daily for four days, and then, e.g., at a reduced dose on day 6, 8, 10 and 12. The treatment can further include administration of one or more additional chemotherapeutic agent. The treatment can further include administration of leucovorin.

Growth Factors for Blood Cells

The polysaccharide preparations described herein can be administered in combination with a chemotherapeutic agent that is administered in combination with growth factors for blood cells (e.g. myeloid cells, granulocytes, and red blood cells) to treat a subject having cancer, e.g., a primary tumor, or having or at risk of having metastasis of a primary tumor. The administration of a chemotherapeutic agent that requires co administration of a growth factor for blood cells (e.g. myeloid cells and red blood cells), e.g., to counter one or more side effect of the chemotherapeutic agent, may be associated with mobilization of bone marrow derived progenitor cells such as endothelial progenitor cells in subjects having cancer.

In one embodiment, the method includes administering the chemotherapeutic agent in combination with a growth factor and then subsequent administration of a polysaccharide preparation described herein. For example, the polysaccharide preparation can be administered one, two, three, five, ten, fifteen, twenty hours, or 1, 2, 3, 4 days after the administration of the growth factor.

Exemplary growth factors include, but are not limited to, colony stimulating factors (e.g., granulocyte colony stimulating factor (GCSF), granulocyte macrophage colony stimulating factor (GM-CSF)), and erythropoietin.

In one embodiment, the subject has one of the following cancers: lung cancer (e.g., small cell lung cancer or non small cell lung cancer), urothelial cancer, a nonmyeloid malignancy, breast cancer, ovarian cancer and a neuroblastoma.

In one embodiment, the subject has lung cancer (e.g., small cell lung cancer or non small cell lung cancer) and the method includes administering an anthracycline (e.g., doxorubicin, daunorubicin, epirubicin, idarubicin, mitoxantrone, valrubicin), a topoisomerase inhibitor (e.g., topotecan, irinotecan, etoposide, teniposide, lamellarin D, SN-38, camptothecin) and/or an alkylating agent (e.g., cyclophosphamide, dacarbazine, melphalan, ifosfamide, temozolomide) in combination with a growth factor (e.g., a colony stimulating factor, e.g., GCSF, GM-CSF), and then subsequently administering a polysaccharide preparation described herein.

In one embodiment, the subject has urothelial cancer and the method includes administering an anthracycline (e.g., doxorubicin, daunorubicin, epirubicin, idarubicin, mitoxantrone, valrubicin), a topoisomerase inhibitor (e.g., topotecan, irinotecan, etoposide, teniposide, lamellarin D, SN-38, camptothecin) and/or an alkylating agent (e.g., cyclophosphamide, dacarbazine, melphalan, ifosfamide, temozolomide) in combination with a growth factor (e.g., a colony stimulating factor, e.g., GCSF, GM-CSF), in combination with a polysaccharide preparation described herein, e.g., concomitantly or serially.

In one embodiment, the subject has a nonmyeloid cancer and the method includes administering an anthracycline (e.g., doxorubicin, daunorubicin, epirubicin, idarubicin, mitoxantrone, valrubicin), a platinum based agent (e.g., cisplatin, carboplatin, oxaliplatin), a vinca alkaloid (e.g., vinblastine, vincristine, vindesine and vinorelbine) and/or an antimetabolite (e.g., methotrexate) in combination with a growth factor (e.g., a colony stimulating factor, e.g., GCSF, GM-CSF), in combination with a polysaccharide preparation described herein, e.g., concomitantly or serially.

In one embodiment, the subject has breast cancer or ovarian cancer and the method includes administering a platinum based agent (e.g., cisplatin, carboplatin, oxaliplatin), a topoisomerase inhibitor (e.g., topotecan, irinotecan, etoposide, teniposide, lamellarin D, SN-38, camptothecin) and/or an alkylating agent (e.g., cyclophosphamide, dacarbazine, melphalan, ifosfamide, temozolomide) in combination with a growth factor (e.g., a colony stimulating factor, e.g., GCSF, GM-CSF), in combination with a polysaccharide preparation described herein, e.g., concomitantly or serially. The breast cancer can be estrogen receptor positive breast cancer; estrogen receptor negative breast cancer; HER-2 positive breast cancer; HER-2 negative breast cancer; progesterone receptor positive breast cancer; progesterone receptor negative breast cancer; estrogen receptor negative, HER-2 negative and progesterone receptor negative breast cancer (i.e., triple negative breast cancer).

In one embodiment, the subject has a neuroblastoma and the method includes administering an anthracycline (e.g., doxorubicin, daunorubicin, epirubicin, idarubicin, mitoxantrone, valrubicin), a platinum based agent (e.g., cisplatin, carboplatin, oxaliplatin) and/or an alkylating agent (e.g., cyclophosphamide, dacarbazine, melphalan, ifosfamide, temozolomide) in combination with a growth factor (e.g., a colony stimulating factor, e.g., GCSF, GM-CSF), and then subsequently administering a polysaccharide preparation described herein.

Radiation and Surgery

The polysaccharide preparations described herein can be administered in combination with radiation therapy or surgery to treat a subject having cancer, e.g., a primary tumor, or having or at risk of having metastasis of a primary tumor. As discussed herein, administration of surgery and/or radiation to a subject having cancer is associated with mobilization of bone marrow derived progenitor cells such as EPCs.

Other Embodiments

This invention is further illustrated by the following examples that should not be construed as limiting. The contents of all references, patents and published patent applications cited throughout this application are incorporated herein by reference.

EXAMPLES

Example 1

Preparation of a Polysaccharide Preparation

This example describes the production of a polysaccharide preparation described herein.

Overview:

Glycol Split low molecular weight heparin alcohol (GS-LMWH-CH$_2$—OH) was generated from unfractionated heparin (UFH) by controlled nitrous acid depolymerization followed by oxidative glycol-splitting and subsequent reduction to an alcohol. In the first step, UFH was depolymerized to obtain depolymerized heparin (DPH-CHO) having an anhydromannose moiety at the reducing end of the polysaccharide. This was followed by Step II oxidative cleavage of the 2,3-diols present in the depolymerized heparin with sodium periodate to generate ring opened glycol split residues along the heparin chain (GS-DPH-CHO). The Step III involved a reduction step, wherein the aldehydic moieties are converted to alcohols using sodium borohydride to generate Glycol Split low molecular weight heparin alcohol.

Method Overview:

The following paragraphs describe the preparation and properties of a polysaccharide preparation described herein.

1. Depolymerization:

Unfractionated Heparin (10 g) was dissolved in 100 mL of de-ionized water equilibrated at room temperature. The pH of this solution was subsequently lowered to pH 3.1, following which sodium nitrite (0.03 M) was added. This reaction solution was allowed to stir for 3 hours following which the pH was neutralized prior to addition of sodium chloride (10 g). After complete dissolution of salt, methanol (200 mL) was added to this solution with constant stirring. The precipitate obtained was then aged at 6° C. for 2 hours. This precipitate was then filtered and dried to obtain DPH in 80-85% yield and possessing the following characteristics:

Mw: 5300-6100
Mw Distribution: (i) <3000 Daltons: 23-30%
(ii) 3000-8000 Daltons: 50-55%
(iii) >8000 Daltons: 15-22%
Anti-Xa Activity: 80-120 IU/mg
Anti-IIa Activity: 40-70 IU/mg 2. Periodate Oxidation The aldehyde (5 g) obtained in Step I was dissolved in 50 mL water equilibrated at 5° C. To this solution was added cooled NaIO$_4$ solution (0.1 M, 50 mL) and the reaction mixture was allowed to stir in the absence of light for 16 hours. On completion, the reaction was quenched by the addition of diethylene glycol (10 mL), following which the temperature was raised back to room temperature. Five grams of sodium chloride was then added to this solution, followed by addition of 150 mL methanol to precipitate the heparin. The precipitate was allowed to age at 6° C. for 2 hours before filtration and drying to yield a glycol-split polysaccharide (95-98% yield) with the following characteristics:

Mw: 5000-5800
Mw Distribution: (i) <3000 Daltons: 25-30%
(ii) 3000-8000 Daltons: 55-60%
(iii) >8000 Daltons: 15-20%

3. Reduction

The glycol split polysaccharide (4 g) obtained above in Step II was dissolved in 40 mL water maintained at 5° C. To this solution was added sodium borohydride (0.4 g) and the reaction mixture subsequently stirred for 1 hour. After 1 hour, the reaction mixture was brought to room temperature, followed by the addition of sodium chloride (4 g). Following salt dissolution, methanol (80 mL) was added to this solution accompanied with constant stirring. The precipitate thus obtained was then allowed to age at 6° C. for 2 hours before filtration and drying to yield the desired product. A polysaccharide preparation with the following characteristics was thus obtained in 55-60% yield:

Mw: 5500-6200
Mw Distribution: (i) <3000 Daltons: 17-23%
(ii) 3000-8000 Daltons: 56-62%
(iii) >8000 Daltons: 17-22%
Anti-Xa Activity: 1-20 IU/mg
Anti-IIa Activity: 1-10 IU/mg Example 2

Preparation of a Polysaccharide Preparation

Depolymerization:

Unfractionated Heparin is dissolved in 10-fold volume of de-ionized water equilibrated at room temperature. The pH of this solution is adjusted to pH 3.1, and sodium nitrite (0.03 M) is added. This reaction solution is allowed to stir for several hours following which the pH is neutralized prior to addition of sodium chloride (same amount as starting UFH material). After complete dissolution of salt, at least 2 volumes of methanol are added to this solution with constant stiffing. The precipitate obtained is aged at about room temperature for about 1 hour. This precipitate is then filtered and dried to obtain DPH in 80-85% typical yield.

Periodate Oxidation:

The aldehyde obtained in Step I is dissolved in about 10 volumes of water equilibrated at 5° C. To this solution is added an equal volume of cooled NaIO$_4$ solution (0.1 M) and the reaction mixture is allowed to stir for 16 hours. On completion, the reaction is quenched by the addition of an alcohol, following which the temperature is raised back to room temperature. Sodium chloride (double the amount as starting aldehyde material) is then added to this solution, followed by addition of at least 3 volumes methanol to precipitate the heparin. The precipitate is allowed to age at about room temperature for 2 hours before filtration and drying to yield a glycol-split polysaccharide (typically about 95-98% yield).

Reduction:

The glycol split polysaccharide obtained in Step II is dissolved in 10 volumes of water maintained at 5° C. To this solution is added sodium borohydride (one tenth the starting amount of GS polysaccharide) and the reaction mixture is subsequently stirred for 1 hour. The reaction mixture is then brought to room temperature, followed by the addition of sodium chloride (same amount as the starting amount of GS polysaccharide). Following salt dissolution, 2 volumes of methanol is added to this solution accompanied with constant stiffing. The precipitate thus obtained is allowed to age at about room temperature before filtration and drying to yield the desired product. A MONC402 LMWH-sodium preparation with the following characteristics is thus obtained in approximately 55-60% yield:
Mw: 5000-7800 Daltons
Mw Distribution: (i) <3000 Daltons: 15-25%
(ii) 3000-8000 Daltons: 55-65%
(iii) >8000 Daltons: 15-25%
Anti-Xa Activity: 1-20 IU/mg
Anti-IIa Activity: 1-20 IU/mg Example 3

Anti-Metastatic Properties of Polysaccharide Preparations

This example shows that the polysaccharide preparations have anti-cancer and anti-metastatic activity in multiple models of metastasis.

Model A: Murine Melanoma Experimental Metastasis (B16F10 iv) Model

A polysaccharide preparation produced as described in Example 1 (herein referred to as "MONC402") showed anti-metastasis activity in a murine melanoma experimental metastasis model.

Female C57BL/6 mice (9-10 weeks old) were treated once with a single dose (10 mg/kg) of MONC402, dalteparin/Fragmin® (a LMWH which has been reported to decrease metastasis), or MONC 202 (negative control, N-desulfated polysaccharide) immediately before i.v. injection of $2 \times 10^5$ B16F10 cells. Mice were sacrificed on day 21 and tumor burden was calculated as lung weight—normal lung weight. As shown in FIG. 1, MONC402 significantly inhibited B16F10 colonization of the lung relative to a pooled (untreated) control.

Model B: Colon Cancer Metastasis to the Liver

MONC402 showed prophylactic anti-metastasis activity in an orthotopic liver metastasis model.

Liver metastasis was initiated by intraperitoneal injection of C170HM2 human colorectal tumor cells into male MF1 nude (nu/nu) athymic mice. 5FU/leucovorin was used as a positive control.

C170HM2 cells were maintained in vitro in RPMI culture medium (Sigma) containing 10% (v/v) heat inactivated fetal bovine serum and 2 mM L-glutamine at 37° C. in 5% $CO_2$ and humidified conditions. Cells from sub-confluent monolayers were harvested with 0.025% EDTA, washed in culture medium and re-suspended in sterile phosphate buffered saline, pH 7.4 (PBS) for in vivo administration. $1.5 \times 10^6$ cells in a volume of 1 ml were injected intraperitoneally into 65 mice, and the mice were allocated into treatment groups as below.

| Group 1: n = 10 | Vehicle control |
|---|---|
| Group 2: n = 10 | 25 mg/kg 5FU/leucovorin i.v. cycled on days 1, 3, 5, 7 |
| Group 3: n = 10 | 5 mg/kg compound 1 (Dalteparin) s.c. once daily |
| Group 4: n = 10 | 5 mg/kg compound 2 (MONC402) s.c. once daily |
| Group 5: n = 10 | 15 mg/kg compound 2 s.c. once daily |
| Group 6: n = 10 | 30 mg/kg compound 2 s.c. once daily |
| Group 7: n = 5 | Untreated |

Treatment was initiated on day 1 following cell injection and continued until day 35 or until the clinical condition of the animal required termination. Groups 5 and 6 missed one dose on day 5. No adverse affects of the test compounds in mice bearing the tumors were observed.

The study was terminated on day 35, and the tumors in the liver were excised and weighed. The numbers of lung nodules are also counted. The mean liver tumor weights and cross-sectional area are summarized in Table 1.

TABLE 1

C170HM2 model: summary of mean liver tumor weight and statistical analysis

| Group | Treatment | Mean tumor weight | | | Mean tumor area | | |
|---|---|---|---|---|---|---|---|
| | | (g) | (% of vehicle) | One way ANOVA | (mm²) | (% of vehicle) | One way ANOVA |
| 1 | Vehicle | 0.097 | 100.00 | — | 34.18 | 100.00 | — |
| 2 | 5FU/Leu | 0.037 | 11.94 | p = 0.006 | 13.12 | 15.7 | p = 0.011 |
| 3 | 5 mg/kg Dalteparin | 0.018 | 18.56 | p = 0.017 | 8.09 | 23/67 | p = 0.031 |
| 4 | 5 mg/kg MONC402 | 0.057 | 58.76 | NS | 18.34 | 53.66 | NS |
| 5 | 15 mg/kg MONC402 | 0.010 | 10.31 | p = 0.007 | 6.95 | 20.33 | p = 0.016 |
| 6 | 30 mg/kg MONC402 | 0.003 | 3.09 | p = 0.004 | 0.96 | 2.80 | p = 0.004 |
| 7 | Untreated control | 0.31 | — | p = 0.035 | 83.58 | 244.53 | p = 0.084 |

NS = not significant

Both 15 mg/kg and 30 mg/kg MONC402 significantly reduced the liver tumor size by 90% (p=0.007) and 97% (p=0.004) respectively and also were significantly more effective than 5FU/leucovorin (p=0.041 and p=0.011, respectively). Dalteparin (group 3) reduced liver tumor weight by approximately 81% (p=0.017) when compared to the vehicle control group. Similarly, the cross-sectional area of the tumors also showed significant reduction with dalteparin (p=0.027) and 15 and 30 mg/kg MONC402 (p=0.016 and p=0.004, respectively).

Mouse weights were monitored for the duration of the study. The mouse weights for each group remained within an acceptable range for all groups throughout the study.

Model C: Breast Cancer Metastasis to the Lung

MONC402 also showed anti-metastasis activity in a syngeneic orthotopic model of breast cancer metastasis (4T1).

Female BALB/c mice 8 weeks of age (WOA) were injected with $8 \times 10^4$ 4T1 cell intra mammary fat pad. Daily treatment with saline or MONC402 with or without weekly treatment of cisplatin started on day 5. Primary tumors were removed on day 9 and weighed.

As shown in Table 2, cisplatin combined with MONC402 (10, 20, 30 mg/kg) showed a statistically significant decrease in lung metastasis compared to saline control group as determined by lung weight and tumor nodule counting (p<0.05, One way ANOVA). Combination therapy groups (Cisplatin+ MONC402 10/20/30 mg/kg) also had lower incidence of mammary tumor regrowth, thoracic cavity tumor metastasis, and weight loss (>2 g) in the last 3 days before termination of the experiment. Combination therapy groups had higher incidence of transient weight loss (>2 g) the week after surgery but recovered in one week.

TABLE 2

4T1 model: macroscopic tumor metastasis counts

| groups | # of mice | Lung tumor nodule #/ animal | Average lung tumor size | Total tumor nodule | Average tumor size | Total tumor volume |
|---|---|---|---|---|---|---|
| Saline | 15 | 6.0 ± 4.7 | 1.4 | 90 | 2.0 | 122.10 |
| Cisplatin | 16 | 5.6 ± 4.4 | 1.41 | 89 | 1.36 | 134.13 |
| MONC402 30 mg/kg | 16 | 8.4 ± 7.0 | 1.19 | 135 | 1.11 | 140.98 |
| Cisplatin + MONC402 30 mg/kg | 16 | 3.1 ± 3.7 | 0.88 | 49 | 0.85 | 28.78 |
| Cisplatin + MONC402 20 mg/kg | 15 | 2.3 ± 2.9 | 0.8 | 34 | 1.0 | 18.66 |
| Cisplatin + MONC402 10 mg/kg | 16 | 2.3 ± 2.5 | 1.41 | 37 | 1.41 | 57.39 |
| untreated | 7 | 12.9 ± 14.0 | 0.98 | 90 | 1.3 | 65.06 |

In a second 4T1 experiment, female BALB/c mice 8 WOA were injected with $8 \times 10^4$ 4T1 cells intra mammary fat pad. Continuous osmotic pump delivery of saline or MONC 402 with weekly treatment of saline or Cisplatin started on day 4. Primary tumors were removed on day 9. There were no significant differences between the groups in primary tumor weight. However, immunohistology analyses showed significant decrease in microvessel density in tumors from mice treated with the combination of Cisplatin and M-ONC 402. The experiment terminated on day 32 and different samples were taken. 6 mice were either found dead or were terminated early due to worsened overall condition.

Figure 2:
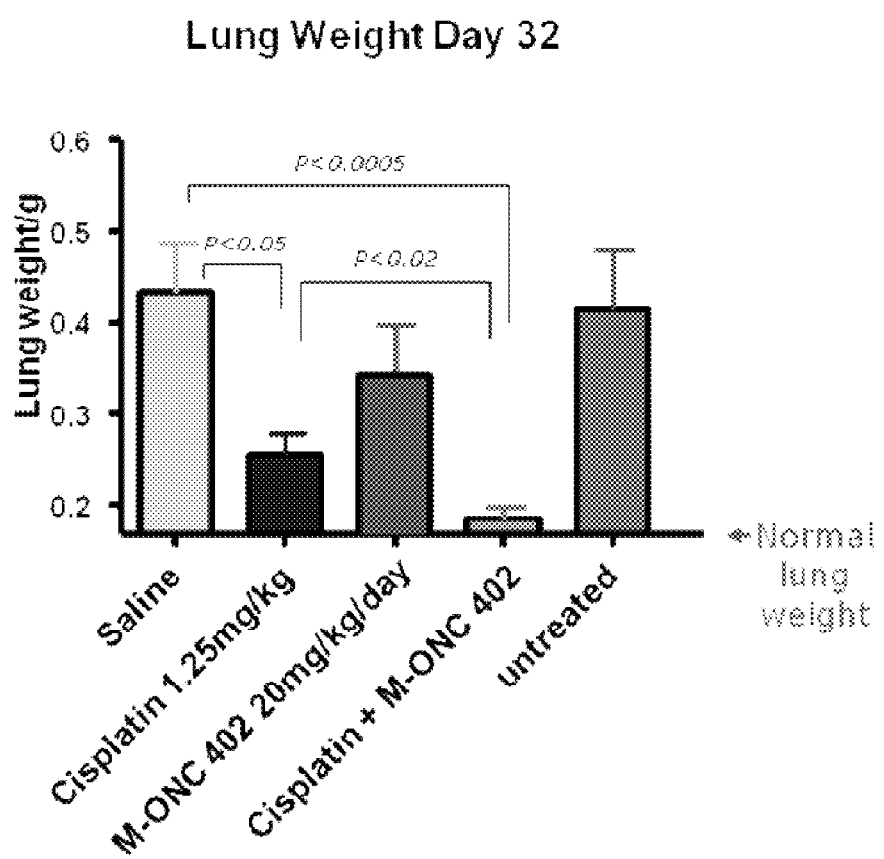
FIG. 2 is a bar graph showing the effect of a polysaccharide preparation described herein in a 4T1 therapeutic model of breast cancer metastasis to the lung. Lung tumor burden (lung weight—normal lung weight) was determined on day 32 for female BALB/c mice (8 weeks old) challenged with intramammary fat pad injection of $8\times10^4$ 4T1 cells and treated as indicated starting on day 4.

4T1 lung metastases were determined by lung weight, lung tumor nodule quantification including nodule number, size and calculated tumor volume, as well as histological quantification. Results are shown in FIG. 2. MONC 402 (20 mg/kg/day) monotherapy groups did not significantly inhibit 4T1 lung metastasis. Cisplatin (1.25 mg/kg) monotherapy showed significant anti-tumor efficacy (p<0.05). The combination of Cisplatin (1.25 mg/kg) with MONC402 (20 mg/kg/day) displayed efficacy in reducing lung metastasis (p<0.0005) and reducing microvessel density. Importantly, the combination therapy group also showed better anti-tumor efficacy when compared to the cisplatin monotherapy group determined by lung weight (p<0.02), tumor nodule number, lung tumor coverage by histology, and lung tumor microvessel density (p<0.05, t-test), demonstrating MONC402 enhanced the anti-tumor efficacy of cisplatin.

Model D: Human Prostate Carcinoma PC-3M Model: Combination Therapy

Male SCID/Beige mice 8 WOA were injected with $5 \times 10^5$ PC-3M-luciferase prostate carcinoma cells intra prostate. Daily treatment with saline or MONC402 with or without weekly treatment of cisplatin started on day 3. Mice were monitored weekly with Xenogen imaging system. The experiment was terminated on day 32. Different organs were isolated and tumor metastasis was assessed by weight and Xenogen imaging.

The MONC402 (30 mg/kg) monotherapy inhibited PC-3M metastasis in the peritoneum. Cisplatin combined with MONC402 (30 mg/kg) decreased tumor growth compared to saline and MONC402 monotherapy groups as determined by in vivo imaging. There was no significant difference between combination therapy (Cisplatin+MONC402 30 mg/kg) and Cisplatin monotherapy in primary tumor weight and metastasis under the specific experimental condition.

Example 4

More Combination Studies and Effect of MONC402 on Mobilization of Cells from Bone Marrow A. MONC402 Effect on Mobilization of Endothelial Progenitor Cells Certain Chemotherapeutic Agents Induce Mobilization of Endothelial Progenitor Cells (EPC). The therapeutic benefits of such agents may be compromised by induction of EPC mobilization that promotes rapid tumor regrowth (see, e.g., Shaked et al., 2008 Cancer Cell, 14: 263-273). The effect of MONC402 given in combination with agents that cause this phenomenon was assessed.

In one experiment, normal mice were treated with G-CSF (s.c., 3 consecutive days), docetaxel or cisplatin (one i.p. dose) with or without simultaneous MONC402 treatment (one s.c. dose). EPC mobilization was monitored 24 h later. Mice (8 mice/group) were dosed s.c. with Saline or MONC402 (40 mg/kg) (or DC101 at 40 mg/kg for control with docetaxel). About 30 min later, mice were given docetaxel (i.p., 40 mg/kg), cisplatin (i.p., 6 mg/kg), or saline control. As a positive control, 2 groups of mice were also dosed with G-CSF i.p. (200 µg/kg) for 3 days, either alone or in combination with a single dose of MONC402 (s.c. at 40 mg/kg) on the last day. 24 h later, the mice were euthanized, and 0.5-0.8 mL of blood taken by cardiac puncture:

About 300 µL of whole blood was transferred directly into 14 mL of lysis buffer for flow cytometry of EPC. The remaining 300-600 µL it were processed for serum (SDF-1α). For flow cytometry, lysed cells were washed and blocked, then stained with CD13-FITC, CD117-PE, 7-AAD, VEGFR2-APC, and CD45-PE/Cy7. A total of 50,000 cells were acquired per sample in the PBMNC gate.

Figure 3:
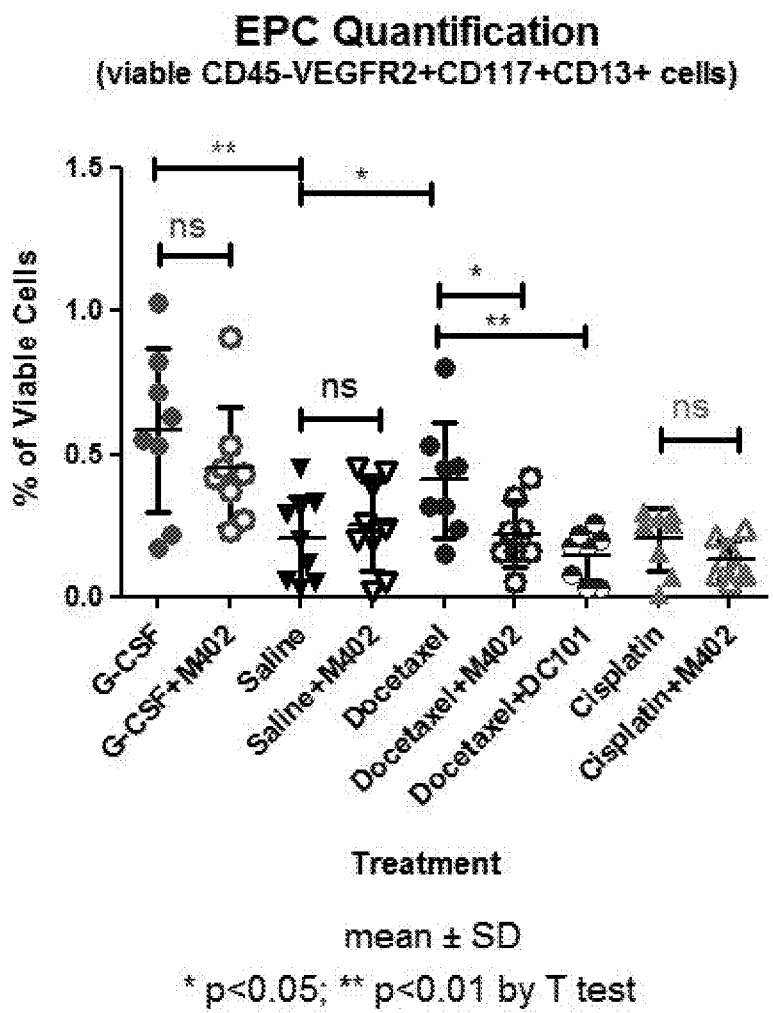
FIG. 3 depicts the effect of MONC402 on G-CSF or docetaxel induced EPC mobilization.

G-CSF and docetaxel induced a significant increase in EPC as compared to the Saline control, while cisplatin treatment did not show this effect. As seen in FIG. 3, docetaxel-induced EPC mobilization was inhibited significantly by DC101

(anti-VEGFR2 Ab) and MONC402. MONC402 did not influence EPC mobilization in saline or cisplatin treated mice. The effect of MONC402 on EPC mobilization with G-CSF was smaller. This illustrates synergistic effects of MONC402 in combination with a taxane and with GCSF.

In a second experiment, it was tested if daily dosing for 5 days with MONC402 would generate a stronger inhibitory effect on EPC mobilization caused by treatment with a taxane.

Mice (10 mice/group) were dosed s.c. with Saline or MONC402 (40 mg/kg), or DC101 (40 mg/kg, as a positive inhibition control with docetaxel). About 30 min later, mice were given docetaxel (i.p., 40 mg/kg) or saline control. As a positive control, 2 groups of mice were also dosed with G-CSF (200 μg/kg) s.c. for 5 consecutive days±daily MONC402. 24 h later, the mice were euthanized, and 500-800 μL of blood taken by cardiac puncture. 150 μL were transferred into 5 mL of lysis buffer for flow cytometric analysis of EPC. The remaining 350-500 μL were processed for serum (SDF-1a). For flow cytometry, cells were washed and blocked and then stained with CD13-FITC, CD117-PE, 7-AAD, VEGFR2-APC, and CD45-PE/Cy7. A total of 50,000 cells were acquired per sample in the PBMNC gate.

Figure 4:
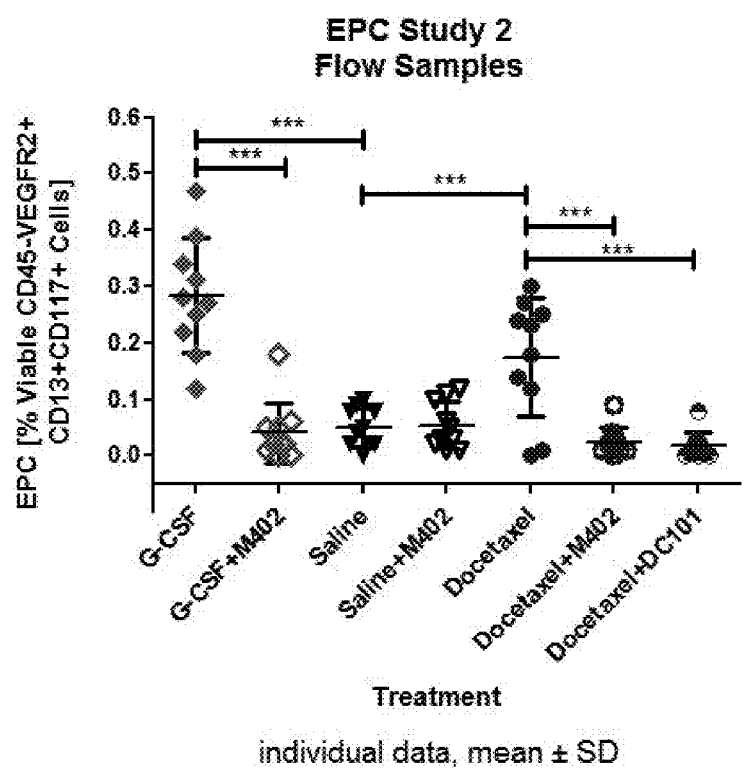
FIG. 4 depicts the effect of MONC402 on G-CSF or docetaxel induced EPC mobilization.

As shown in FIG. 4, G-CSF and Docetaxel induced a significant increase in EPC mobilization, and both could be inhibited by MONC402. MONC402 was equivalent to DC101 (anti-VEGFR2 Ab) in inhibiting the docetaxel induced EPC mobilization. MONC402 did not influence EPC mobilization in saline treated mice, indicating that MONC402 does not suppress normal EPC generation or release, but may interfere with mechanisms induced by docetaxel. Again, this shows MONC402's synergistic effects in combination with agents that induce EPC mobilization.

A third experiment was conducted to evaluate the effect of MONC402 on EPC mobilization in response to treatment with docetaxel in 4T1 tumor bearing mice. The study also evaluated if EPC mobilization could be inhibited by MONC402 administered via osmotic pump.

4T1 tumors were implanted on Day 0 at $1\times10^5$ cells/mouse into the $4^{th}$ mammary fat pad. Pumps with Saline or MONC402 were implanted on Day 0, immediately after tumor cell injections. Mice were randomized to the following groups:

1. Saline Control, n=8
2. Docetaxel, 40 mg/kg, Day 6, n=8
3. M402, pump, 40 mg/kg/day, Day 0, n=8
4. Docetaxel, 40 mg/kg, Day 6+M402, pump, 40 mg/kg/day, Day 0, n=8

Docetaxel or Saline was administered i.p. on Day 6 in the AM. Four h later, mice were bled by submandibular plexus for EPC profiling and soluble factor analysis. Primary tumors were removed on Day 9 for histological analyses. Blood was also collected for soluble factor analyses (72 h after docetaxel dosing). Serum samples were analyzed using a 19-plex Luminex kit. In addition, samples were also tested for SDF-1a levels by ELISA. SDF-1a was chosen because it is a heparin-binding protein; publications showed an increase in this chemokine upon docetaxel treatment and SDF-1a is involved in recruiting bone marrow stem cells to new sites. MONC402 and the combination of MONC402 with Docetaxel had a small, non-significant impact on tumor weight.

Figure 5:
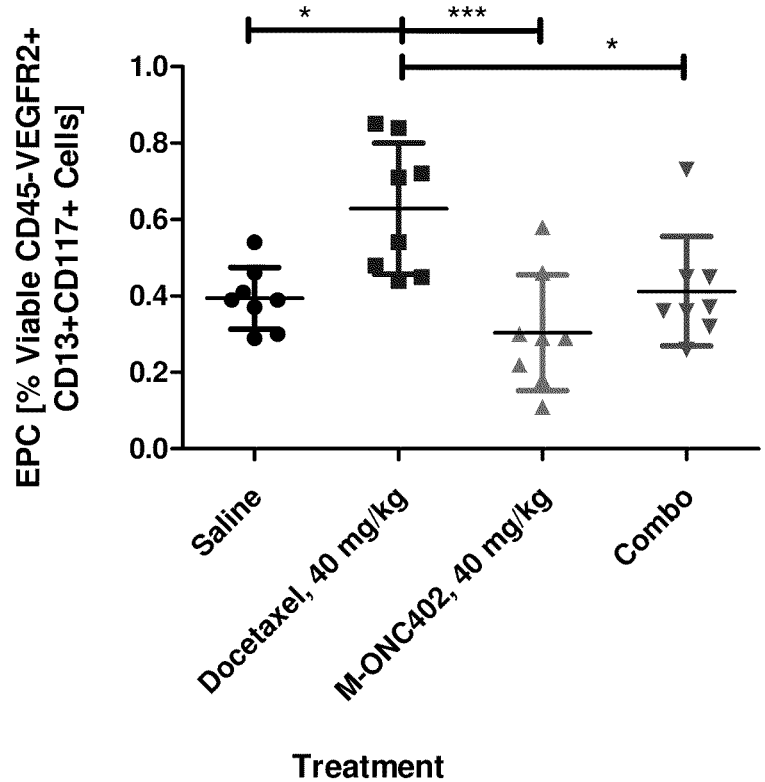
FIG. 5 depicts the effect of MONC402 on docetaxel induced EPC mobilization in tumor-bearing mice.

Docetaxel induced a significant increase in EPC in the blood by 4 h at the 40 mg/kg dose, as observed in previous studies. MONC402 monotherapy, delivered via osmotic pump at 40 mg/kg/day did not induce significant changes in mobilized EPC; however, a trend toward reduced EPC levels was observed. As shown in FIG. 5, the co-administration of MONC402 by continuous osmotic pump significantly inhibited the blood EPC mobilization by docetaxel and reduced the levels to those of the saline control in 7 of 8 mice. These results confirm the observations from the previous studies, this time conducted in tumor-bearing mice and by administering MONC402 via osmotic pump. Taken together, these data suggest that a single docetaxel dose mobilizes EPC into the blood, which can be inhibited with concurrent MONC402 treatment at 40 mg/kg/day.

B. MONC402 Effect on Mobilization of G-CSF Induced MDSC Mobilization

The effect of MONC402 on mobilization of other cells from the bone-marrow was assessed.

Figure 6:
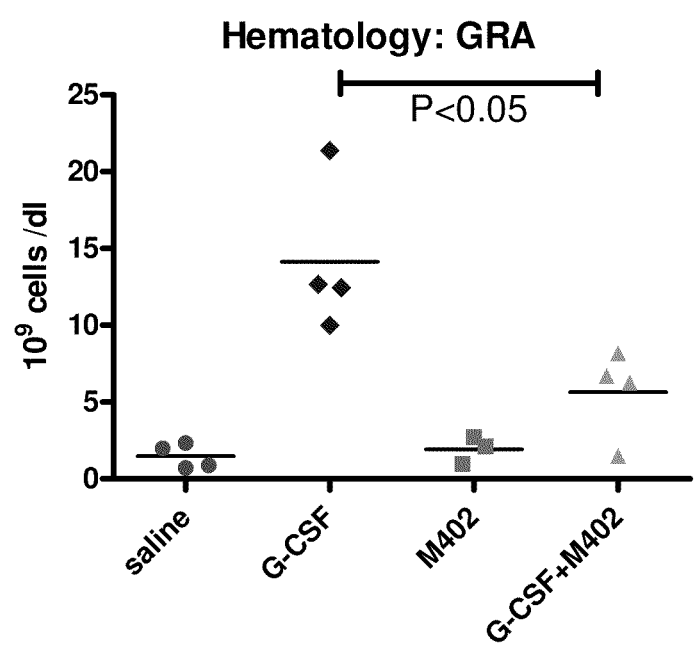
FIG. 6 depicts the effect of G-CSF on MSDC mobilization.

BALB/c mice were treated with 4 daily doses of sc saline or G-CSF at 0.5 mg/kg, in combination with sc MONC402 (20 mg/kg). Animals were sacrificed on day 5, blood samples saved by cardiac puncture. Hematology analyses were performed with VetScan HM2. Granulocytes (GRA) are defined by size and granularity, and >90% were $CD11b^+GR-1^+$ when analyzed by flow cytometry. As shown in FIG. 6, MONC402 inhibited G-CSF induced mobilization of MDSC.

C. Effect of Combination with Tyrosine Kinase Inhibitors

This example tested the effect of MONC402 in combination with a tyrosine kinase inhibitor used in treatment of cancer: sunitinib (Sutent®) at two different time points. A dose of sunitinib at 90 mg/kg was chosen as it effectively mobilized EPC without causing toxicity in this mouse model.

Accelerated tumor invasion and metastasis after short term sunitinib treatment is reported in the literature (Ebos et al. 2009. *Cancer Cell* 15: 232-239). Surprisingly, as described below, the addition of MONC402 to the sunitinib treatment significantly inhibited EPC mobilization and reduced the aggressive regrowth phenotype in tumor-bearing mice. While not bound by theory, analysis of EPC in the bone marrow suggests that MONC402 may prevent the egress of bone marrow progenitor cells into circulation.

In one experiment, 36 Balb/c female mice were treated daily with vehicle or 90 mg/kg sunitinib (8 mice per group). Sunitinib was administered orally as a suspension in vehicle (0.5% carboxy methyl cellulose, 0.4% Tween 80, 1.8% NaCl). MONC402 (20 mg/kg for a 20 g mouse) was administered s.c. twice daily.

| | | | |
|---|---|---|---|
| Group # 1 | N = 8 | Vehicle (0.1 ml p.o. opd) | Saline (0.2 ml s.c. bid) |
| Group # 2 | N = 8 | Sunitinib 90 mg/kg (0.1 ml p.o. opd) | Saline (0.2 ml s.c. bid) |
| Group # 3 | N = 8 | Vehicle (0.1 ml p.o. opd) | MONC402 20 mg/kg (0.2 ml s.c. bid) |
| Group # 4 | N = 8 | Sunitinib 90 mg/kg (0.1 ml p.o. opd) | MONC402 20 mg/kg (0.2 ml s.c. bid) |

On day 7 four mice in each group were sacrificed 2 hours after the last dose of sunitinib and MONC402. Whole blood was collected for EPC isolation as well as sera and bone marrow from one femur for each mouse. Isolation and FACS analysis of EPCs was done. Sera was separated and stored at −80° C. until Luminex analysis or SDF-1a or SCF ELISA.

On day 8 four mice in each group were sacrificed 24 hours after the last dose of sunitinib and MONC402. Whole blood was collected for EPC isolation as well as sera and bone marrow from one femur for each mouse. Isolation and FACS analysis of EPCs was done. Sera was separated and stored at −80° C. until Luminex analysis or SDF-1a or Stem Cell Factor (SCF) ELISA.

Sunitinib induced a significant increase in EPC in the blood by 2 h. This increase was transient and resolved by 24 h in this study. MONC402 monotherapy at 20 mg/kg BID did not induce significant changes at 2 h or 24 h in blood EPC. At 2 h, the addition of MONC402 to the sunitinib treatment significantly inhibited the blood EPC mobilization and reduced the levels to those of the saline control in 2 of 4 mice. Both sunitinib and sunitinib in combination with MONC402 induced a significant increase in the production of EPC in the bone marrow at 2 h, which was significantly higher in the mice receiving sunitinib and MONC402. By 24 h, the percentage of EPC in the bone marrow was normalized in the group receiving sunitinib and close to the saline control in the group receiving sunitinib and MONC402. No increase in the production of EPC in the bone marrow was observed at 2 h or 24 h for mice treated with MONC402 alone.

Taken together, the data suggest that sunitinib treatment for 7 days mobilizes EPC into the blood, which can be inhibited with concurrent MONC402 treatment at 20 mg/kg BID. While not bound by theory, MONC402 may act via trapping the induced EPC in the bone marrow.

A second experiment was performed to demonstrate the effect of MONC402 on sunitinib (Sutent®) induced EPC mobilization in tumor-bearing mice.

Luciferase-transfected MB-231-3P cells were implanted into 20 cages of 8-9 week old female Fox-Chase SCID mice at a concentration of $7 \times 10^5$ cells/60 µL/mouse on Day 0. Primary tumor volume was monitored through Day 21. Tumors were resected and weighed on Day 25. Mice were randomized into 4 groups:

Vehicle control

Sunitinib (60 mg/kg once a day for 7 days, po)

MONC402 (20 mg/kg twice a day for 7 days, sc)

Combo therapy (sunitinib and MONC402)

Animals in which primary tumors had attached to or penetrated the abdominal muscle or where the abdominal muscle was compromised during surgery were not used in this experiment. Treatment commenced on Day 26, one day after primary tumor resection. Each morning, sunitinib or vehicle was administered to all animals via oral gavage. MONC402 or saline was then administered via subcutaneous injection. Animals were again administered MONC402 or saline later in the afternoon. Sunitinib was prepared fresh daily by suspending the contents of one (1) 50 mg capsule in 8.3 mL vehicle. Sunitinib was resuspended by vortex before gavaging each animal. Wet food was provided daily to all animals. Tumors were resected on Day 25 and treatment began on Day 26.

Mice were bled via submandibular plexus 24 h after the last sunitinib dose and one drop of blood collected into RBC lysis buffer. Cells were washed twice with FACS buffer and stained with: anti-CD13-FITC, anti-CD117-PE, 7-AAD, anti-VEGFR-2-APC and anti-CD45-PE/Cy7 for 20 min at 2-8° C. Cells were washed again and fixed in 2% formaldehyde. Samples were analyzed on the FACS Canto the following day.

Figure 7:
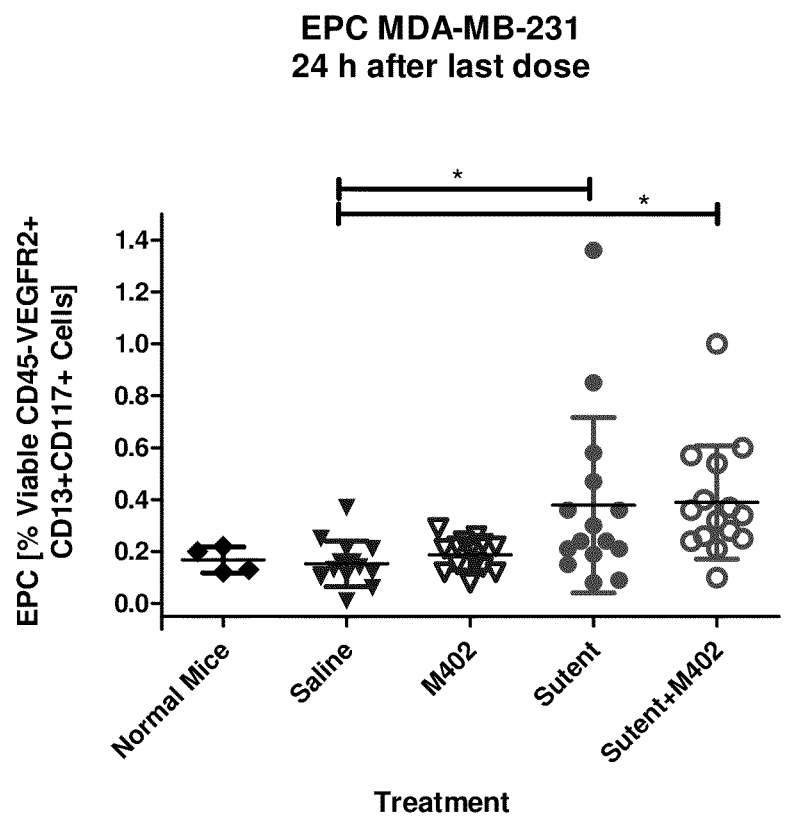
FIG. 7 depicts effect of sunitinib (Sutent®) on EPC mobilization.

Sunitinib monotherapy showed a modest but significant increase in circulating EPC 24 h after dosing. The increase was not as pronounced as observed with the higher (120 mg/kg) Sunitinib dose in normal mice and was mainly driven by 4 mice with higher percentages. MONC402 treatment did not increase the percentage of circulating EPC as compared to the saline control. The combination of MONC402 with sunitinib resulted in circulating EPC levels similar to the sunitinib alone group, again driven by 4 mice with higher percentages. See FIG. 7.

Figure 8:
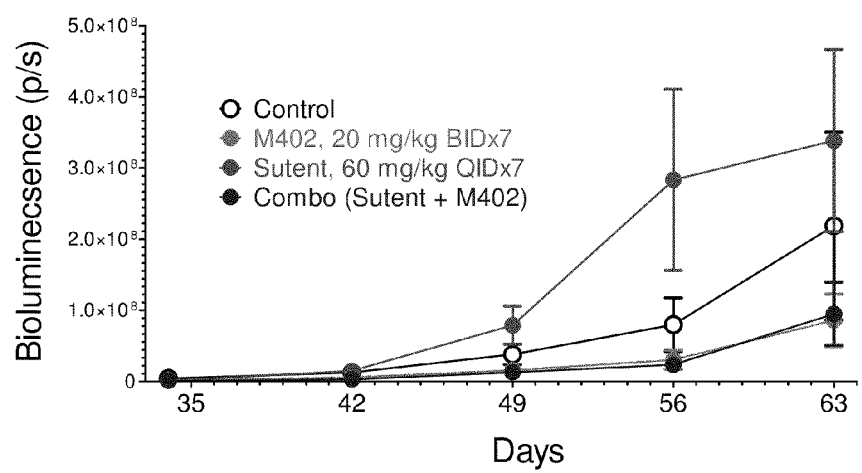
FIG. 8 is a graph depicting the effect of MONC402 on sunitinib (Sutent®)-induced accelerated tumor regrowth and metastasis.

In a third experiment, Luciferase-transfected MB-231-3P cells were implanted into 21 cages of 10-11 week old female Fox-Chase SCID mice at a concentration of $1 \times 10^6$ cells/50 µL/mouse on Day 0. The effect of MONC402 on Sutent-induced accelerated tumor regrowth and metastasis was evaluated. Primary tumor volume was monitored through Day 21. Tumors were resected on Day 24 after implant at which time tumors were 316.9±11.1 mm$^3$. Mice with lower body weight (≤17-18 g) were excluded from the study. Animals were subsequently randomized into 1 of 4 groups: (1) Vehicle control; (2) Sutent (60 mg/kg QD×7 po); (3) M402 (20 mg/kg BID×7 sc); (4) Combo therapy (Sutent QD+M402 BID). Treatments commenced on Day 26, two days after primary tumor resection, and were given for 7 consecutive days. Mice received no further treatment thereafter and were monitored for tumor progression by bioluminescent imaging and survival. FIG. 8 depicts whole body bioluminescence over time (Mean±SEM, n=16). Sutent treated animal displayed significantly accelerated tumor progression (primary tumor re-growth and metastasis) when compared to saline control group (P<0.05, One-way ANOVA with Newman-Keuls multiple comparison test). M402 treated animals did not show significant changes in tumor progression when compared to saline control. Most importantly, when M402 was given together with Sutent, it significantly delayed tumor progression when compared to Sutent monotherapy group (P<0.05, One-way ANOVA with Newman-Keuls multiple comparison test).

A number of embodiments of the invention have been described. Nevertheless, it will be understood that various modifications may be made without departing from the spirit and scope of the invention. Accordingly, other embodiments are within the scope of the following claims.

What is claimed is:

1. A method of lessening, reducing, mitigating, ameliorating, or delaying pancreatic cancer in a subject, comprising administering to the subject a pharmaceutical composition comprising a polysaccharide preparation having the following characteristics:
    (a) a weight average chain molecular weight between 3,500 and 8,000 Da;
    (b) anti-Xa activity of less than 20 IU/mg and anti-IIa activity of 1 IU/mg or less;
    (c) greater than 5% and less than 25% glycol split uronic acid residues; and
    (d) a molecular weight distribution such that 10-40% of the polysaccharides of the preparation have a molecular weight <3000 Da; 45-65% of the polysaccharides have a molecular weight between 3000-8000 Da, and 15-30% of the polysaccharides have a molecular weight >8000 Da, wherein, the preparation comprises polysaccharides of Formula I:

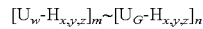

wherein each occurrence of U indicates a uronic acid residue and each occurrence of H indicates a hexosamine residue;
wherein m and n are integers such that
m=4-16, and
n=1-4;
each of w, x, y and z can independently be the same or different for each occurrence of [U$_w$-H$_{x,y,z}$] and each of x, y and z can independently be the same or different for each occurrence of [U$_G$-H$_{x,y,z}$], wherein
w=-2OS or -2OH;
x=—NS or —NAc;

y=-3OS or -3OH;
z=-6OS or -6OH;
and

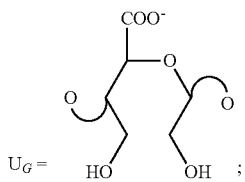

wherein the symbol ~ indicates that the units marked m and n are distributed along the polysaccharide chain and are not necessarily in sequence.

2. The method of claim 1, wherein the polysaccharide preparation has an anti-Xa activity of less than 15 IU/mg.

3. The method of claim 1, wherein the polysaccharide preparation has an anti-Xa activity of less than 10 IU/mg.

4. The method of claim 1, wherein the preparation has greater than 5% and less than 20% glycol split uronic acid residues.

5. The method of claim 1, wherein the preparation has between 10% and 20% glycol split uronic acid residues.

6. The method of claim 1, wherein the preparation has greater than 40% $U_{2S}H_{NS,6S}$ disaccharide residues.

7. The method of claim 6, wherein the preparation has greater than 70% $U_{2S}H_{NS,6S}$ disaccharide residues.

8. The method of claim 6, wherein the preparation has a degree of desulfation less than 40%.

9. The method of claim 6, wherein the preparation has a degree of desulfation less than 30%.

10. The method of claim 6, wherein the preparation has a degree of desulfation less than 10%.

11. The method of claim 1, wherein the reducing end further comprises a 2,5-anhydromannitol residue.

12. The method of claim 1, wherein the polysaccharides of the preparation have a uronic acid at the non-reducing end.

13. The method of claim 1, wherein the polysaccharides of the preparation have a non native uronic acid at the non-reducing end.

14. The method of claim 1, wherein the polysaccharides of the preparation have a glycol split uronic acid at the non-reducing end.

15. The method of claim 1, wherein n=1-3.

16. The method of claim 1, wherein the pancreatic cancer is a metastatic cancer.

17. The method of claim 1, wherein the preparation is administered intravenously.

18. The method of claim 1, wherein the preparation is administered subcutaneously.

19. The method of claim 1, wherein the preparation is administered daily.

20. The method of claim 1, wherein the preparation is administered in combination with a second therapy.

21. The method of claim 20, wherein the second therapy comprises administration of one or more therapeutic agents.

22. The method of claim 21, wherein the therapeutic agent is a cytotoxic or cytostatic agent or a combination thereof.

23. The method of claim 21, wherein the one or more therapeutic agent is gemcitabine.

24. The method of claim 23, further comprising administering abraxane in combination with the polysaccharide preparation and the gemcitabine.

25. A method of lessening, reducing, mitigating, ameliorating, or delaying pancreatic cancer in a subject, the method comprising administering a polysaccharide preparation having anti-Xa activity of less than 20 IU/mg and anti-IIa activity of 1 IU/mg or less; greater than 5% and less than 25% glycol split uronic acid residues; a plurality of polysaccharide chains of the preparation having a glycol split uronic acid residue ($U_G$), wherein, the plurality of polysaccharide chains of the preparation each have no more than 3 glycol split uronic acid residues ($U_G$); and the polysaccharide preparation has a molecular weight distribution such that 10-40% of the oligosaccharides of the preparation have a molecular weight <3000 Da; 45-65% of the oligosaccharides have a molecular weight between 3000-8000 Da, and 15-30% of the oligosaccharides have a molecular weight >8000 Da, wherein, the preparation comprises polysaccharides of Formula I:

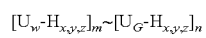

wherein each occurrence of U indicates a uronic acid residue and each occurrence of H indicates a hexosamine residue;
wherein m and n are integers such that
m=4-16, and
n=1-4:
each of w, x, y and z can independently be the same or different for each occurrence of $[U_w\text{-}H_{x,y,z}]$ and each of x, y and z can independently be the same or different for each occurrence of $[U_G\text{-}H_{x,y,z}]$, wherein
w=-2OS or -2OH;
x=—NS or —NAc;
y=-3OS or -3OH;
z=-6OS or -6OH;
and

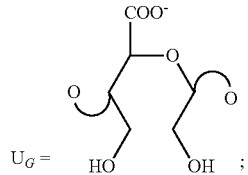

wherein the symbol ~ indicates that the units marked m and n are distributed along the polysaccharide chain and are not necessarily in sequence.

26. The method of claim 25, wherein the polysaccharide preparation has an anti-Xa activity of less than 15 IU/mg.

27. The method of claim 25, wherein the polysaccharide preparation has an anti-Xa activity of less than 10 IU/mg.

28. The method of claim 25, wherein the plurality of polysaccharide chains of the preparation each have no more than 2 glycol split uronic acid residues ($U_G$).

29. The method of claim 28, wherein the plurality of polysaccharide chains of the preparation each have no more than 1 glycol split uronic acid residue ($U_G$) per polysaccharide chain.

30. The method of claim 25, wherein the reducing end further comprises a 2,5-anhydromannitol residue.

31. The method of claim 25, wherein the polysaccharides of the preparation have a uronic acid at the non-reducing end.

32. The method of claim 25, wherein the polysaccharides of the preparation have a non native uronic acid at the non-reducing end.

33. The method of claim 25, wherein the polysaccharides of the preparation have a glycol split uronic acid at the non-reducing end.

34. The method of claim 25, wherein n=1-3.

35. The method of claim 25, wherein the pancreatic cancer is a metastatic cancer.

36. The method of claim 25, wherein the preparation is administered intravenously.

37. The method of claim 25, wherein the preparation is administered subcutaneously.

38. The method of claim 25, wherein the preparation is administered daily.

39. The method of claim 25, wherein the preparation is administered in combination with a second therapy.

40. The method of claim 39, wherein the second therapy comprises administration of one or more therapeutic agents.

41. The method of claim 40, wherein the therapeutic agent is a cytotoxic or cytostatic agent or a combination thereof.

42. The method of claim 40, wherein the one or more therapeutic agent comprises gemcitabine.

43. The method of claim 42, further comprising administering abraxane in combination with the polysaccharide preparation and the gemcitabine.

44. A method of lessening, reducing, mitigating, ameliorating, or delaying pancreatic cancer in a subject, comprising administering to the subject a pharmaceutical composition comprising a polysaccharide preparation having the following characteristics:
  (a) a weight average chain molecular weight between 3,500 and 8,000 Da;
  (b) a molecular weight distribution such that 10-40% of the polysaccharides of the preparation have a molecular weight <3000 Da; 45-65% of the polysaccharides have a molecular weight between 3000-8000 Da, and 15-30% of the polysaccharides have a molecular weight >8000 Da;
  (c) greater than 5% and less than 25% glycol split uronic acid residues;
  (d) anti-Xa activity of less than 15 IU/mg and anti-IIa activity of 1 IU/mg or less, wherein, the preparation comprises polysaccharides of Formula I:

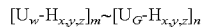

wherein each occurrence of U indicates a uronic acid residue and each occurrence of H indicates a hexosamine residue;
wherein m and n are integers such that
m=4-16, and
n=1-3;
each of w, x, y and z can independently be the same or different for each occurrence of $[U_w\text{-}H_{x,y,z}]$ and each of x, y and z can independently be the same or different for each occurrence of $[U_G\text{-}H_{x,y,z}]$, wherein
w=-2OS or -2OH;
x=—NS or —NAc;
y=-3OS or -3OH;
z=-6PS or -6OH;
and

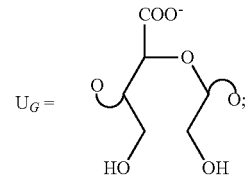

wherein the symbol ~ indicates that the units marked m and n are distributed along the polysaccharide chain and are not necessarily in sequence; and
wherein a plurality of the polysaccharides on the preparation have a 2,5-anhydromannitol residue at the reducing end and non native uronic acid at the non-reducing end.

45. The method of claim 44, further comprising administering the pharmaceutical composition in combination with gemcitabine.

46. The method of claim 45, further comprising administering abraxane in combination with the gemcitabine.

* * * * *